US011544407B1

(12) United States Patent
Sjöstrand

(10) Patent No.: US 11,544,407 B1
(45) Date of Patent: Jan. 3, 2023

(54) SYSTEMS AND METHODS FOR SECURE CLOUD-BASED MEDICAL IMAGE UPLOAD AND PROCESSING

(71) Applicant: Progenics Pharmaceuticals, Inc., N. Billerica, MA (US)

(72) Inventor: Karl Vilhelm Sjöstrand, New York, NY (US)

(73) Assignee: Progenics Pharmaceuticals, Inc., N. Billerica, MA (US)

( * ) Notice: Subject to any disclaimer, the term of this patent is extended or adjusted under 35 U.S.C. 154(b) by 72 days.

(21) Appl. No.: 17/032,667

(22) Filed: Sep. 25, 2020

Related U.S. Application Data

(60) Provisional application No. 62/907,168, filed on Sep. 27, 2019.

(51) Int. Cl.
*G06F 21/62* (2013.01)
*H04L 9/40* (2022.01)
(Continued)

(52) U.S. Cl.
CPC ........ *G06F 21/6254* (2013.01); *G06F 3/0482* (2013.01); *G06F 16/5866* (2019.01); *G16H 30/20* (2018.01); *H04L 63/20* (2013.01)

(58) Field of Classification Search
CPC ............... G06F 21/6254; G06F 3/0482; G06F 16/5866; G16H 30/20; H04L 63/20
See application file for complete search history.

(56) References Cited

U.S. PATENT DOCUMENTS

| | | | |
|---|---|---|---|
| 8,199,985 | B2 | 6/2012 | Jakobsson et al. |
| 8,211,401 | B2 | 7/2012 | Babich et al. |

(Continued)

FOREIGN PATENT DOCUMENTS

| | | |
|---|---|---|
| CN | 101528267 A | 9/2009 |
| CN | 102361594 A | 2/2012 |

(Continued)

OTHER PUBLICATIONS

Anand, A. et al., A Pre-Analytical Validation Study of Automated Bone Scan Index: Effect on Accuracy and Reproducibility Due to the Procedural Variabilities in Bone Scan Image Acquisition. J Nucl Med, pp. 1865-1871, (2016).
Anand, A. et al., Analytic Validation of the Automated Bone Scan Index as an Imaging Biomarker to Standardize Quantitative Changes in Bone Scans of Patients with Metastatic Prostate Cancer, J. Nucl. Med., 57(1):41-45 (2016).

(Continued)

*Primary Examiner* — Hien L Duong
(74) *Attorney, Agent, or Firm* — Choate, Hall & Stewart LLP; William R. Haulbrook; Ronen Adato

(57) ABSTRACT

Presented herein are systems and methods that facilitate user review and uploading of files comprising medical images and associated metadata from a local computing device to a network-based image analysis and/or decision support platform. The systems and methods described herein allow image upload to be performed in a secure fashion that prevents the network-based platform from accessing sensitive data as it is prepared for upload. Prior to file upload, sensitive data elements are flagged and their values removed and/or masked. Notably, the approaches described herein provide intuitive graphical user interface (GUI) tools that allow a user, such as a medical practitioner or researcher, to review not only the images and metadata in the files that they plan to upload, but also to review and control the process by which sensitive data elements are removed and/masked, thereby confirming that all files are free of sensitive information prior to upload.

23 Claims, 30 Drawing Sheets

(51) Int. Cl.
*G06F 3/0482* (2013.01)
*G06F 16/58* (2019.01)
*G16H 30/20* (2018.01)

(56) References Cited

U.S. PATENT DOCUMENTS

| | | |
|---|---|---|
| 8,778,305 B2 | 7/2014 | Pomper et al. |
| 8,855,387 B2 | 10/2014 | Hamadeh et al. |
| 8,962,799 B2 | 2/2015 | Babich et al. |
| 9,002,081 B2 | 4/2015 | Brown |
| 9,721,340 B2 | 8/2017 | Gillies et al. |
| 10,311,971 B2 | 6/2019 | Opfer et al. |
| 10,339,653 B2 | 7/2019 | Gillies et al. |
| 10,340,044 B2 | 7/2019 | Yao et al. |
| 10,340,046 B2 | 7/2019 | Baker |
| RE47,609 E | 9/2019 | Hamadeh et al. |
| 10,600,184 B2 | 3/2020 | Golden et al. |
| 10,665,346 B2 | 5/2020 | Baker |
| 10,748,652 B2 | 8/2020 | Yao et al. |
| 10,762,993 B2 | 9/2020 | Baker |
| 10,867,697 B2 | 12/2020 | Lyman et al. |
| 10,869,608 B2 | 12/2020 | Dormer et al. |
| 10,916,337 B2 | 2/2021 | Poblenz et al. |
| 10,973,486 B2 | 4/2021 | Sjostrand et al. |
| 11,238,968 B1* | 2/2022 | Farr .................. G16H 20/10 |
| 11,321,844 B2 | 5/2022 | Johnsson et al. |
| 2006/0062425 A1 | 3/2006 | Shen et al. |
| 2007/0081712 A1 | 4/2007 | Huang et al. |
| 2010/0215581 A1 | 8/2010 | Hoffmann |
| 2013/0129168 A1 | 5/2013 | Ross |
| 2013/0208955 A1* | 8/2013 | Zhao .................. G16Z 99/00 382/128 |
| 2013/0208966 A1* | 8/2013 | Zhao .................. G06Q 40/08 709/219 |
| 2015/0110716 A1 | 4/2015 | Armor |
| 2015/0331995 A1 | 11/2015 | Zhao et al. |
| 2016/0203263 A1 | 7/2016 | Maier et al. |
| 2016/0335395 A1* | 11/2016 | Wu .................. G16H 30/20 |
| 2017/0083682 A1 | 3/2017 | McNutt et al. |
| 2018/0144828 A1 | 5/2018 | Baker |
| 2018/0259608 A1 | 9/2018 | Golden et al. |
| 2019/0209116 A1 | 7/2019 | Sjostrand et al. |
| 2020/0027559 A1 | 1/2020 | Baker |
| 2020/0085382 A1 | 3/2020 | Taerum et al. |
| 2020/0126666 A1 | 4/2020 | Baker |
| 2020/0143084 A1* | 5/2020 | Rosenberg .......... H04L 67/12 |
| 2020/0152299 A1* | 5/2020 | Rosenberg .......... G16H 30/20 |
| 2020/0160976 A1 | 5/2020 | Lyman et al. |
| 2020/0193603 A1 | 6/2020 | Golden et al. |
| 2020/0245960 A1 | 8/2020 | Richter et al. |
| 2020/0285771 A1* | 9/2020 | Dey .................. G06F 21/6272 |
| 2020/0337658 A1 | 10/2020 | Sjostrand et al. |
| 2020/0342600 A1 | 10/2020 | Sjostrand et al. |
| 2020/0357118 A1* | 11/2020 | Yao .................. G06V 10/774 |
| 2020/0357521 A1 | 11/2020 | Baker |
| 2020/0373003 A1* | 11/2020 | Lyman .............. A61B 5/7275 |
| 2021/0012883 A1 | 1/2021 | Bidulock et al. |
| 2021/0093249 A1 | 4/2021 | Anand et al. |
| 2021/0335041 A1* | 10/2021 | Haslam .............. G06N 3/08 |

FOREIGN PATENT DOCUMENTS

| | | |
|---|---|---|
| EP | 1426903 A2 | 6/2004 |
| EP | 3043318 A1 | 7/2016 |
| JP | 6013042 B2 | 10/2016 |
| JP | 6170284 B2 | 7/2017 |
| SE | 524500 C2 | 8/2004 |
| WO | WO-99/05503 A2 | 2/1999 |
| WO | WO-2009/084995 A1 | 7/2009 |
| WO | WO-2011/077303 A1 | 6/2011 |
| WO | WO-2015/058151 A2 | 4/2015 |
| WO | WO-2018/081354 A1 | 5/2018 |
| WO | WO-2019/103912 A2 | 5/2019 |
| WO | WO-2019/136349 A2 | 7/2019 |
| WO | WO-2020/144134 A1 | 7/2020 |
| WO | WO-2020/190821 A1 | 9/2020 |
| WO | WO-2020/219619 A1 | 10/2020 |
| WO | WO-2020/219620 A1 | 10/2020 |
| WO | WO-2021/061315 A1 | 4/2021 |

OTHER PUBLICATIONS

Anand, A. et al., Automated Bone Scan Index as a quantitative imaging biomarker in metastatic castration-resistant prostate cancer patients being treated with enzalutamide, EJNMMI Research, 6:23, 7 pages (2016). .
Belal, S. L. et al, 3D skeletal uptake of $^{18}$F sodium fluoride in PET/CT images is associate with overall survival in patients with prostate cancer, EJNMMI Research, 7(15):1-8 (2017).
Bushberg, J. T. et al., Essential Physics of Medical Imaging, Essential Physics of Medical Imaging, 19.3: p. 581 (table 15-3), p. 713 paragraph 6, section 19.3 and p. 720, (2011).
Eiber, M. et al., Prostate Cancer Molecular Imaging Standardized Evaluation (PROMISE): Proposed miTNM Classification for the Interpretation of PSMA-Ligand PET/CT, The Journal of Nuclear Medicine, 59(3):469-478, (2018).
Giesel, F. L et al., F-18 labelled PSMA-1007: biodistribution, radiation dosimetry and histopathological validation of tumor lesions in prostate cancer patients, Eur. J. Nucl. Med. Mol. Imaging, 44:678-688 (2017).
Gjertsson, K., Segmentation in Skeletal Scintigraphy Images using Convolutional Neural Networks, Master's Theses in Mathematical Sciences, pp. 39-58, (2017), <https://lup.lub.lu.se/student-papers/search/publication/8916406>.
Goffin, K. E et al., Phase 2 study of $^{99m}$Tc-trofolastat SPECT/CT to identify and localize prostate cancer in intermediate- and high-risk patients undergoing radical prostatectomy and extended pelvic lymph node dissection, J. Nucl. Med., 27 pages (2017).
Hiller, S. M. et al., 99mTc-Labeled Small-Molecule Inhibitors of Prostate-Specific Membrane Antigen for Molecular Imaging of Prostate Cancer, Journal of Nuclear Medicine, 54(8):1369-1376 (2013) retrieved Oct. 25, 2017: <http://jnm.snmjournals.org/content/54/8/1369.full>.
Horikoshi, H. et al., Computer-aided diagnosis system for bone scintigrams from Japanese patients: importance of training database, Annals of Nuclear Medicine, 26(8):622-626 (2012).
Kaboteh R. et al., Progression of bone metastases in patients with prostate cancer—automated detection of new lesions and calculation of bone scan index, EJNMMI Research, 3:64, 6 pages (2013).
Kiess, et al., Prostate-specific membrane antigen and a target for cancer imaging and therapy, The Quarterly Journal of Nuclear Medicine and Molecular Imaging, 59(3):241-268 (2015).
Kopka, K. et al., Glu-Ureido-Based Inhibitors of Prostate-Specific Membrane Antigen: Lessons Learned During the Development of a Novel Class of Low-Molecular-Weight Theranostic Radiotracers, The Journal of Nuclear Medicine, 58(9)(Suppl. 2):17S-26S, (2017).
Liu, L. et al., Computer-Aided Detection of Prostate Cancer with MRI: Technology and Applications, Acad Radiol. Author manuscript, 50 pp. 2016.
Ma, L. et al., Automatic segmentation of the prostate on CT images using deep learning and multi-atlas fusion, Proc. of SPIE vol. 10133:101332O-1-101332O-9 (2017).
Ma, L. et al., Combining Population and Patient-Specific Characteristics for Prostate Segentation on 3D CT Images, Proc of SPIE 9784:978427-1-8 (2016).
Ma, L. et al., Random Walk Based Segmentation for the Prostate on 3D Transrectal Ultrasound Images, Proc SPIE Int Soc Opt Eng. Author manuscript, 13 pages (2016).
Nakajima, K. et al., Enhanced diagnostic accuracy for quantitative bone scan using an artificial neural network system: a Japanese multi-center database project, EJNMMI Research, 3:83, 9 pages, (2013).
Ohlsson, M., et al., Automated decision support for bone scintigraphy, Computer-based medical systems, pp. 1-6, (2009).
Rowe, S. P. et al., PET Imaging of prostate-specific membrane antigen in prostate cancer: current state of the art and future challenges, Prostate Cancer and Prostatic Diseases, pp. 1-8 (2016).

(56) References Cited

OTHER PUBLICATIONS

Rowe, S. P. et al., PSMA-Based [$^{18}$F]DCFPyL PET/CT is Superior to Conventional Imaging for Lesion Detection in Patients with Metastatic Prostate Cancer, Mol Imaging Biol, 18:411-419, (2016).
Sadik, M. et al., A new computer-based decision-support system for the interpretation of bone scans, Nuclear Medicine Communications, 27(5):417-423 (2006).
Sajn, L. et al., Computerized segmentation of whole-body bone scintigrams and its use in automated diagnostics, Computer Methods and Programs in Biomedicine, 80:47-55 (2005).
Santos-Cuevas, C. et al. 99mTc-labeled PSMA inhibitor: Biokinetics and radiation dosimetry in healthy subjects and imaging of prostate cancer tumors in patients, Nuclear Medicine and Biology 52:1-6, (2017).
Sjöstrand, K., et al., Automated detection and quantification of Prostatic PSMA uptake in SPECT/CT using a Deep Learning Algorithm for Segmentation of Pelvic Anatomy, The Journal of Nuclear Medicine, 59(1):p. 30, (2018).
Sjostrand, K., et al., Automated Assessment of Prostatic PSMA Expression in SPECT/CT using Deep Convolutional Neural Networks—A Prospectively Planned Retrospective Analysis of Phase 3 Study MIP-1404-3301, The Journal of Nuclear Medicine, 60 (Supplement 1): Abstract 401, 1 page, (2019).
Tian, Z. et al., A fully automatic multi-atlas based segmentation method for prostate MR images, Proc SPIE Int Soc Opt Eng. Author manuscript, 12 pages (2015).
Tian, Z. et al., A supervoxel-based segmentation method for prostate MR images, Med. Phys., 44(2):558-569 (2017).
Tian, Z. et al., Deep convolutional neural network for prostate MR segmentation, Proc. of SPIE 10135:101351L-1-101351L-6 12 pages, (2017).
Tian, Z., et al., Superpixel-based Segmentation for 3D Prostate MR Images, IEEE Trans Med Imaging, Author manuscript, pp. 558-569, (2016).
Trägärdh, E., et al., RECOMIA-a cloud-based platform for artificial intelligence research in nuclear medicine and radiology, EJNMMI Physics, <https://doi.org/10.1186/s40658-020-00316-9>, 7:51, 12 pages, (2020).
Ulmert, D. et al., A Novel Automated Platform for Quantifying the Extent of Skeletal Tumour Involvement in Prostate Cancer Patients Using the Bone Scan Index, European Urology, 62(1):78-84 (2012).
Yin, T.-K., and Chiu, N.T., A Computer-Aided Diagnosis for Locating Abnormalities in Bone Scintigraphy by a Fuzzy System With a Three-Step Minimization Approach, IEEE Transactions on Medical Imaging, 23(5):639-654 (2004).

\* cited by examiner

SYSTEMS AND METHODS FOR SECURE CLOUD-BASED MEDICAL IMAGE UPLOAD AND PROCESSING

CROSS-REFERENCE TO RELATED APPLICATION

This application claims priority to and benefit of U.S. Provisional Application No. 62/907,168, filed Sep. 27, 2019, the content of which is hereby incorporated by reference in its entirety.

FIELD OF THE INVENTION

This invention relates generally to methods and systems, for analysis and/or presentation of medical image data. More particularly, in certain embodiments, the invention relates to methods and systems for facilitating transfer of medical image data to cloud-based platforms.

BACKGROUND OF THE INVENTION

Targeted image analysis involves the use of radiolabeled small molecules that bind to specific receptors, enzymes and proteins in the body that are altered during the evolution of disease. After administration to a patient, these molecules circulate in the blood until they find their intended target. The bound radiopharmaceutical remains at the site of disease, while the rest of the agent clears from the body. The radioactive portion of the molecule serves as a beacon so that an image may be obtained depicting the disease location and concentration using commonly available nuclear medicine cameras, known as single-photon emission computerized tomography (SPECT) or positron emission tomography (PET) cameras, found in most hospitals throughout the world. Physicians can then use this information to determine the presence and the extent of disease in a patient. The physician can use this information to provide a recommended course of treatment to the patient and to track the progression of disease.

There are a variety of software-based analytical techniques available for analysis and enhancement of PET and SPECT images that can be used by a radiologist or physician. There are also a number of radiopharmaceuticals available for imaging particular kinds of cancer. Imaging agents used in the art include, among others include, without limitation $^{18}$F-NaF, $^{11}$C-Choline, 2-deoxy-2 [18F] fluoro-d-glucose (FDG), and the like. For example, the small molecule diagnostic 1404 targets the extracellular domain of prostate specific membrane antigen (PSMA), a protein amplified on the surface of >95% of prostate cancer cells and a validated target for the detection of primary and metastatic prostate cancer. 1404 is labeled with technetium-99 m, a gamma-emitter isotope that is widely available, relatively inexpensive, facilitates efficient preparation, and has spectrum characteristics attractive for nuclear medicine imaging applications.

Another example radiopharmaceutical is PyL™ (also known as [$^{18}$F]DCFPyL, and 18F-PyL), which is a clinical-stage, fluorinated PSMA-targeted PET imaging agent for prostate cancer. A proof-of-concept study published in the April 2016 issue of the Journal of Molecular Imaging and Biology demonstrated that PET imaging with PyL™ showed high levels of PyL™ uptake in sites of putative metastatic disease and primary tumors, suggesting the potential for high sensitivity and specificity in detecting prostate cancer.

An oncologist may use images from a targeted PET or SPECT study of a patient as input in her assessment of whether the patient has a particular disease, e.g., prostate cancer, what stage of the disease is evident, what the recommended course of treatment (if any) would be, whether surgical intervention is indicated, and likely prognosis. The oncologist may use a radiologist report in this assessment. A radiologist report is a technical evaluation of the PET or SPECT images prepared by a radiologist for a physician who requested the imaging study and includes, for example, the type of study performed, the clinical history, a comparison between images, the technique used to perform the study, the radiologist's observations and findings, as well as overall impressions and recommendations the radiologist may have based on the imaging study results. A signed radiologist report is sent to the physician ordering the study for the physician's review, followed by a discussion between the physician and patient about the results and recommendations for treatment.

Thus, the process involves having a radiologist perform an imaging study on the patient, analyzing the images obtained, creating a radiologist report, forwarding the report to the requesting physician, having the physician formulate an assessment and treatment recommendation, and having the physician communicate the results, recommendations, and risks to the patient. The process may also involve repeating the imaging study due to inconclusive results, or ordering further tests based on initial results.

If an imaging study shows that the patient has a particular disease or condition (e.g., cancer), the physician discusses various treatment options, including surgery, as well as risks of doing nothing or adopting a watchful waiting or active surveillance approach, rather than having surgery.

There are limitations associated with this process, both from the perspective of the physician and from the perspective of the patient. While the radiologist's report is certainly helpful, the physician must ultimately rely on her experience in formulating an assessment and recommendation for her patient. Furthermore, the patient must place a great deal of trust in his physician. The physician may show the patient his PET/SPECT images and may tell the patient a numerical risk associated with various treatment options or likelihood of a particular prognosis, but the patient may very well struggle to make sense of this information. Moreover, the patient's family will likely have questions, particularly if cancer is diagnosed but the patient opts not to have surgery. The patient and/or his family members may search online for supplemental information and may become misinformed about risks of the diagnosed condition. A difficult ordeal may become more traumatic.

Thus, there remains a need for systems and methods for improved automated analysis of medical imaging studies and communication of those results, diagnoses, prognoses, treatment recommendations, and associated risks to a patient.

SUMMARY OF THE INVENTION

Presented herein are systems and methods that facilitate user review and uploading of files comprising medical images and associated metadata from a local computing device to a network-based image analysis and/or decision support platform. The systems and methods described herein allow image upload to be performed in a secure fashion that prevents the network-based platform from accessing sensitive data as it is prepared for upload. Prior to file upload, sensitive data elements are flagged and their values removed and/or masked. Notably, the approaches described herein provide intuitive graphical user interface (GUI) tools that allow a user, such as a medical practitioner or researcher, to review not only the images and metadata in the files that they plan to upload, but also to review and control the process by which sensitive data elements are removed and/masked, thereby confirming that all files are free of sensitive information prior to upload.

In the context of medical images, where patient privacy is paramount, this process allows a user, such as a medical practitioner, to ensure that uploaded files are free of any data that could be used to ascertain identity of a particular patient. By allowing a user to securely and confidently interact with cloud-based platforms that can dramatically facilitate data analysis, collaboration, and communication of results, the interactive tools for data upload described herein offer key functionality facilitating medical image analysis.

In one aspect, the invention is directed to a method for secure upload of one or more (e.g., a plurality of) medical images and associated metadata from a local computing device to a network-based (e.g., a cloud-based) analysis and/or decision support platform, the method comprising: (a) causing, by a processor of the local computing device, display of a graphical user interface (GUI) for user review and management of medical image upload; (b) receiving, by the processor of the local computing device (e.g., via the GUI), a user selection of one or more files for upload, wherein each of the one or more files for upload comprises one or more medical image(s) and associated metadata comprising a plurality of data elements [e.g., that convey information about the associated medical image, such as information about a particular patient (e.g., the imaged patient), a particular study that the image was collected as part of, imaging parameters (e.g., the imaging modality), and the like], and wherein each selected file (of the one or more files for upload) is stored on the local computing device (e.g., that is not part of the network-based (e.g., a cloud-based) analysis and/or decision support platform); (c) accessing, by the processor of the local computing device, for each selected file, the associated metadata of the file and identifying, among the plurality of data elements of the associated metadata, one or more flagged data elements for de-identification prior to upload; (d) creating, by the processor of the local computing device, for each selected file, de-identified metadata corresponding to the associated metadata of the file with values of the flagged data elements removed and/or masked (e.g., replaced with a masking value that obscures the original value and/or conveys more limited information); (e) receiving, by the processor of the local computing device (e.g., via the GUI), a user selection of a particular file for review of de-identification; (f) responsive to the user selection of the particular file, causing, by the processor of the local computing device, (e.g., via the GUI) display of a graphical representation of metadata changes comprising a listing of the plurality of data elements of the associated metadata of the particular file and a visual indication of the one or more flagged data elements (e.g., identifying flagged data elements in particular colors, text formatting, etc. so as to visually distinguish from other data elements, placing color coded icons/indicators in proximity to flagged data elements, etc.); (g) receiving, by the processor of the local computing device, a user confirmation to upload; and (h) (e.g., responsive to the receipt of the user confirmation to upload) uploading, by the processor of the local computing device, each selected file with the original associated metadata replaced with the corresponding de-identified metadata, to the network-based platform.

In certain embodiments, the method comprises: (i) causing, by the processor, (e.g., via the GUI; e.g., responsive to receipt of a user input to display de-identified metadata) display of a graphical representation of the de-identified metadata that corresponds to the associated metadata of the particular file.

In certain embodiments, the method comprises: (j) causing, by the processor, (e.g., via the GUI; e.g., responsive to receipt of a user input to display original metadata) display of a graphical representation of original associated metadata of the particular file (e.g., without the visual indication of the one or more flagged data elements).

In certain embodiments, at least a portion of the flagged data elements are identified as elements to be masked by, for each element to be masked, replacing an initial value of the element to be masked with a particular masking value, and wherein the graphical representation of metadata changes further comprises, for each element to be masked, an indication of the initial value of the element and an indication of the particular masking value for the element.

In certain embodiments, in the graphical representation of metadata changes, the listing of the plurality of data elements of the associated metadata is displayed in a table [(e.g., each data element displayed in a row, with an indication of its value) (e.g., wherein each flagged data element is identified via a colored indicator (e.g., a red indicator displayed next to elements to be removed and/or masked) (e.g., wherein, for each particular data element identified as elements to be masked, an additional row showing the masking value for that particular data element included below the row for that particular data element)].

In certain embodiments, at least a portion of the flagged data elements are identified as elements to be masked (e.g., as opposed to removed) and wherein step (c) comprises, for each element to be masked, replacing an initial value of the element to be masked with a particular masking value.

In certain embodiments, step (c) comprises accessing, by the processor, a stored de-identification protocol comprising a listing of data elements to flag.

In certain embodiments, the method further comprises: receiving, by the processor, (e.g., via the GUI), a user selection of one or more additional data elements to flag for de-identification; and updating, by the processor, the de-identified set of metadata associated with each medical image to remove and/or mask a value of each selected additional data element.

In certain embodiments, the one or more flagged data elements comprise one or more members selected from the group consisting of: a patient name, a patient identifier [e.g., a unique (e.g., numeric or alphanumeric) identifier assigned to the patient], a patient birth date.

In certain embodiments, the local computing device is in communication [e.g., connected to via data acquisition/instrument control hardware and/or channels, such as USB, serial, Ethernet/local area network (LAN), general purpose interface bus (GPIB), etc.; e.g., in communication over a network (e.g., a local private network)] with an imaging system [e.g., a computed tomography (CT) scanner; e.g., a magnetic resonance imaging (MRI) scanner; e.g., a positron emission tomography (PET) scanner; e.g., a single photon emission computed tomography (SPECT) scanner; e.g., a gamma camera scanner (e.g., a scintigraphy imaging scanner); e.g., a combined CT/PET, CT/SPECT, MRI/PET, MRI/SPECT scanner].

In certain embodiments, the local computing device on a local network (e.g., a private, limited access network, such as a network of a hospital or group of hospitals, a network of a research organization, and the like) that is not part of the network-based (e.g., a cloud-based) analysis and/or decision support platform.

In certain embodiments, the method comprises: following step (b), performing, by the processor of the local computing device, a pre-processing step to validate each of the one or more selected files for upload (e.g., to confirm that each selected file comprises a medical image of a particular type and/or format).

In certain embodiments: the pre-processing step comprises identifying, for each file, a corresponding study to which the file belongs, thereby identifying one or more processed studies; and the method comprises causing, by the processor of the local computing device, display of (e.g., via the GUI) a graphical representation of processed studies comprising a listing of the one or more processed studies [e.g., wherein the processed studies are displayed in tabular format with each processed study shown in a different row].

In certain embodiments, the graphical representation of processed studies comprises, for each processed study, a visual indication of a number of different files (e.g., a rendered numerical value in a row) of the study along with a visual indication of one or more imaging modalities used to obtain medical images of the files belonging to the study (e.g., rendered text and/or icons representing particular imaging modalities).

In certain embodiments, the method comprises: receiving, by the processor of the local computing device, a user input to review images of a particular study; and causing, by the processor of the local computing device, display of (e.g., via the GUI) a first medical image of a first file and corresponding to (e.g., obtained using) a particular imaging modality, along with a graphical control element that allows the user to view additional images (i) of files belong to the particular study and (ii) also corresponding to the particular imaging modality (e.g., thereby allowing the user to conveniently scroll through images of the particular study and corresponding to the particular imaging modality).

In another aspect, the invention is directed to a system for secure upload of one or more (e.g., a plurality of) medical images and associated metadata from a local computing device to a network-based (e.g., a cloud-based) analysis and/or decision support platform, the system comprising: a processor of the local computing device (e.g., not part of the network-based platform); and a memory having instructions stored thereon, wherein the instructions, when executed by the processor, cause the processor to: (a) cause display of a graphical user interface (GUI) for user review and management of medical image upload; (b) receive (e.g., via the GUI), a user selection of one or more files for upload, wherein each of the one or more files for upload comprises one or more medical image(s) and associated metadata comprising a plurality of data elements [e.g., that convey information about the associated medical image, such as information about a particular patient (e.g., the imaged patient), a particular study that the image was collected as part of, imaging parameters (e.g., the imaging modality), and the like], and wherein each selected file (of the one or more files for upload) is stored on the local computing device (e.g., that is not part of the network-based (e.g., a cloud-based) analysis and/or decision support platform); (c) access, for each selected file, the associated metadata of the file and identifying, among the plurality of data elements of the associated metadata, one or more flagged data elements for de-identification prior to upload; (d) create, for each selected file, de-identified metadata corresponding to the associated metadata of the file with values of the flagged data elements removed and/or masked (e.g., replaced with a masking value that obscures the original value and/or conveys more limited information); (e) receive (e.g., via the GUI), a user selection of a particular file for review of de-identification; (f) responsive to the user selection of the particular file, cause (e.g., via the GUI) display of a graphical representation of metadata changes comprising a listing of the plurality of data elements of the associated metadata of the particular file and a visual indication of the one or more flagged data elements (e.g., identifying flagged data elements in particular colors, text formatting, etc. so as to visually distinguish from other data elements, placing color coded icons/indicators in proximity to flagged data elements, etc.); (g) receive a user confirmation to upload; and (h) (e.g., responsive to the receipt of the user confirmation to upload) upload each selected file with the original associated metadata replaced with the corresponding de-identified metadata, to the network-based platform.

In certain embodiments, the instructions cause the processor to: (i) cause (e.g., via the GUI; e.g., responsive to receipt of a user input to display de-identified metadata) display of a graphical representation of the de-identified metadata that corresponds to the associated metadata of the particular file.

In certain embodiments, the instructions cause the processor to: (j) cause (e.g., via the GUI; e.g., responsive to receipt of a user input to display original metadata) display of a graphical representation of original associated metadata of the particular file (e.g., without the visual indication of the one or more flagged data elements).

In certain embodiments, at least a portion of the flagged data elements are identified as elements to be masked by, for each element to be masked, replacing an initial value of the element to be masked with a particular masking value, and wherein the graphical representation of metadata changes further comprises, for each element to be masked, an indication of the initial value of the element and an indication of the particular masking value for the element.

In certain embodiments, in the graphical representation of metadata changes, the listing of the plurality of data elements of the associated metadata is displayed in a table [(e.g., each data element displayed in a row, with an indication of its value) (e.g., wherein each flagged data element is identified via a colored indicator (e.g., a red indicator displayed next to elements to be removed and/or masked) (e.g., wherein, for each particular data element identified as elements to be masked, an additional row showing the masking value for that particular data element included below the row for that particular data element)].

In certain embodiments, at least a portion of the flagged data elements are identified as elements to be masked (e.g., as opposed to removed) and wherein at step (c), the instructions cause the processor to, for each element to be masked, replace an initial value of the element to be masked with a particular masking value.

In certain embodiments, at step (c) the instructions cause the processor to access a stored de-identification protocol comprising a listing of data elements to flag.

In certain embodiments, the instructions cause the processor to: receive (e.g., via the GUI), a user selection of one or more additional data elements to flag for de-identification; and update the de-identified set of metadata associated with each medical image to remove and/or mask a value of each selected additional data element.

In certain embodiments, the one or more flagged data elements comprise one or more members selected from the group consisting of: a patient name, a patient identifier [e.g., a unique (e.g., numeric or alphanumeric) identifier assigned to the patient)], a patient birth date.

In certain embodiments, the local computing device is in communication (e.g., connected to via data acquisition/instrument control hardware and/or channels, such as USB, serial, Ethernet/local area network (LAN), general purpose interface bus (GPIB), etc.; e.g., in communication over a network (e.g., a local private network)] with an imaging system [e.g., a computed tomography (CT) scanner; e.g., a magnetic resonance imaging (MRI) scanner; e.g., a positron emission tomography (PET) scanner; e.g., a single photon emission computed tomography (SPECT) scanner; e.g., a gamma camera scanner (e.g., a scintigraphy imaging scanner); e.g., a combined CT/PET, CT/SPECT, MRI/PET, MRI/SPECT scanner]. In certain embodiments, the system further comprising the imaging system.

In certain embodiments, the local computing device is on a local network (e.g., a private, limited access network, such as a network of a hospital or group of hospitals, a network of a research organization, and the like) that is not part of the network-based (e.g., a cloud-based) analysis and/or decision support platform.

In certain embodiments, the instructions cause the processor to: following step (b), perform a pre-processing step (e.g., a pre-processing software routine) to validate each of the one or more selected files for upload (e.g., to confirm that each selected file comprises a medical image of a particular type and/or format).

In certain embodiments, the instructions cause the processor to: identify, for each file, a corresponding study to which the file belongs, thereby identifying one or more processed studies; and cause display of (e.g., via the GUI) a graphical representation of processed studies comprising a listing of the one or more processed studies [e.g., wherein the processed studies are displayed in tabular format with each processed study shown in a different row].

In certain embodiments, the graphical representation of processed studies comprises, for each processed study, a visual indication of a number of different files (e.g., a rendered numerical value in a row) of the study along with a visual indication of one or more imaging modalities used to obtain medical images of the files belonging to the study (e.g., rendered text and/or icons representing particular imaging modalities).

In certain embodiments, the instructions cause the processor to: receive a user input to review images of a particular study; and cause display of (e.g., via the GUI) a first medical image of a first file and corresponding to (e.g., obtained using) a particular imaging modality, along with a graphical control element that allows the user to view additional images (i) of files belong to the particular study and (ii) also corresponding to the particular imaging modality (e.g., thereby allowing the user to conveniently scroll through images of the particular study and corresponding to the particular imaging modality).

In another aspect, the invention is directed to a method for interactive display of data representing medical imaging studies uploaded to a network-based (e.g., a cloud-based) analysis and/or decision support platform via a graphical user interface (GUI), the method comprising: (a) accessing, by a processor of a computing device (e.g., of the network-based platform), a data table comprising, for each of a plurality of study summary variables, a set of values of the study summary variable, each value of the set associated with a particular medical imaging study previously uploaded to (e.g., now stored on) the network-based platform, wherein the study summary variables comprise one or more members selected from the group consisting of: a prior therapy value (e.g., a binary value representing whether or not a particular patient has had prior prostate cancer therapy), a prostate cancer indication [e.g., a value (e.g., an integer; e.g., an enumerated data-type; e.g., a character or string) representing one of a set of indications for categorizing a patient and/or their cancer status, such as screening, recurrent, suspected recurrence, newly-diagnosed, metastatic, and other], a prostate-specific antigen (PSA) test level (e.g., a numeric value), and an imaging modality [e.g., a value (e.g., an integer; e.g., an enumerated data-type; e.g., a character or string) representing one of a set of imaging modalities (e.g., CT, PET, SPECT, MRI, bone-scan, etc.)]; (b) causing, by the processor (e.g., of the network-based platform), display of a graphical user interface (GUI) comprising: (i) a plurality of graphical filter control elements, each graphical filter control element corresponding to a particular study summary variable and providing for a user selection of a sub-range (e.g., selected the sub-range may be, but is not necessarily, a continuous range and, for variables having discrete or enumerated values, may be a list of possible values) of values of the particular study summary variable; and (ii) a plurality of graphical data representations, each graphical data representation corresponding to a study summary variable and providing a visual representation of distribution of the set of values of the study summary variable in the data table (e.g., a bar graph; e.g., a pie chart; e.g., a histogram); (c) receiving, by the processor (e.g., of the network-based platform), via a particular graphical filter control element, a user selection of a sub-range for values of the corresponding particular study summary variable, and using the selected sub-range as a filter to identify, within the data table, for each specific study summary variable, a filtered sub-set of values of the specific study summary variable comprising only those values that are associated with uploaded medical imaging studies which are themselves also associated with those values of the particular study summary variable falling within the selected sub-range; and (d) causing, by the processor (e.g., of the network-based platform), graphical rendering (e.g., for display) of an updated version of the each of the graphical data representations, each providing a visual representation of distribution of values in the filtered sub-set of the corresponding study summary variable (e.g., and causing, by the processor, display of, via the GUI, the updated versions of the graphical data representations).

In certain embodiments, the method comprises performing step (c) repeatedly, for a plurality of different graphical filter control elements to use sub-ranges of multiple study summary variables as filters.

In another aspect the invention is directed to a system for interactive display of data representing medical imaging studies uploaded to a network-based (e.g., a cloud-based) analysis and/or decision support platform via a graphical user interface (GUI), the system , the system comprising: a processor of a computing device; and a memory having instructions stored thereon, wherein the instructions, when executed by the processor, cause the processor to: (a) access, a data table comprising, for each of a plurality of study summary variables, a set of values of the study summary variable, each value of the set associated with a particular medical imaging study previously uploaded to (e.g., now stored on) the network-based platform, wherein the study summary variables comprise one or more members selected from the group consisting of: a prior therapy value (e.g., a binary value representing whether or not a particular patient has had prior prostate cancer therapy), a prostate cancer indication [e.g., a value (e.g., an integer; e.g., an enumerated data-type; e.g., a character or string) representing one of a set of indications for categorizing a patient and/or their cancer status, such as screening, recurrent, suspected recurrence, newly-diagnosed, metastatic, and other], a prostate-specific antigen (PSA) test level (e.g., a numeric value), and an imaging modality [e.g., a value (e.g., an integer; e.g., an enumerated data-type; e.g., a character or string) representing one of a set of imaging modalities (e.g., CT, PET, SPECT, MRI, bone-scan, etc.)]; (b) cause display of a graphical user interface (GUI) comprising: (i) a plurality of graphical filter control elements, each graphical filter control element corresponding to a particular study summary variable and providing for a user selection of a sub-range (e.g., selected the sub-range may be, but is not necessarily, a continuous range and, for variables having discrete or enumerated values, may be a list of possible values) of values of the particular study summary variable; and (ii) a plurality of graphical data representations, each graphical data representation corresponding to a study summary variable and providing a visual representation of distribution of the set of values of the study summary variable in the data table (e.g., a bar graph; e.g., a pie chart; e.g., a histogram); (c) receive, via a particular graphical filter control element, a user selection of a sub-range for values of the corresponding particular study summary variable, and using the selected sub-range as a filter to identify, within the data table, for each specific study summary variable, a filtered sub-set of values of the specific study summary variable comprising only those values that are associated with uploaded medical imaging studies which are themselves also associated with those values of the particular study summary variable falling within the selected sub-range; and (d) cause graphical rendering (e.g., for display) of an updated version of the each of the graphical data representations, each providing a visual representation of distribution of values in the filtered sub-set of the corresponding study summary variable (e.g., and causing, by the processor, display of, via the GUI, the updated versions of the graphical data representations).

In certain embodiments, the instructions cause the processor to perform step (c) repeatedly, for a plurality of different graphical filter control elements to use sub-ranges of multiple study summary variables as filters.

Features of embodiments described with respect to one aspect of the invention may be applied with respect to another aspect of the invention.

BRIEF DESCRIPTION OF THE DRAWING

The foregoing and other objects, aspects, features, and advantages of the present disclosure will become more apparent and better understood by referring to the following description taken in conjunction with the accompanying drawing, in which:

FIG. 3A is another screenshot of the GUI shown in FIG. 1A, showing another view of the pop-up window, comprising a graphical representation of metadata associated with a specific medical image, according to an illustrative embodiment;

FIG. 3B is another screenshot of the GUI shown in FIG. 1A, showing another view of the pop-up window, comprising a graphical representation of metadata associated with a specific medical image, according to an illustrative embodiment;

FIG. 3C is another screenshot of the GUI shown in FIG. 1A, showing another view of the pop-up window, comprising a graphical representation of metadata associated with a specific medical image, according to an illustrative embodiment;

FIG. 3D is another screenshot of the GUI shown in FIG. 1A, showing another view of the pop-up window, comprising a graphical representation of metadata associated with a specific medical image, according to an illustrative embodiment;

FIG. 4A is another screenshot of the GUI shown in FIG. 1A, showing a view that allows a user to enter supplemental data, according to an illustrative embodiment;

FIG. 4B is another screenshot of the view of the GUI shown in FIG. 4A, showing entered supplemental data, according to an illustrative embodiment;

FIG. 4C is another screenshot of the view of the GUI shown in FIG. 4A, showing a pop-up window prompting a user to confirm entered supplemental data, according to an illustrative embodiment;

Figure 6A:
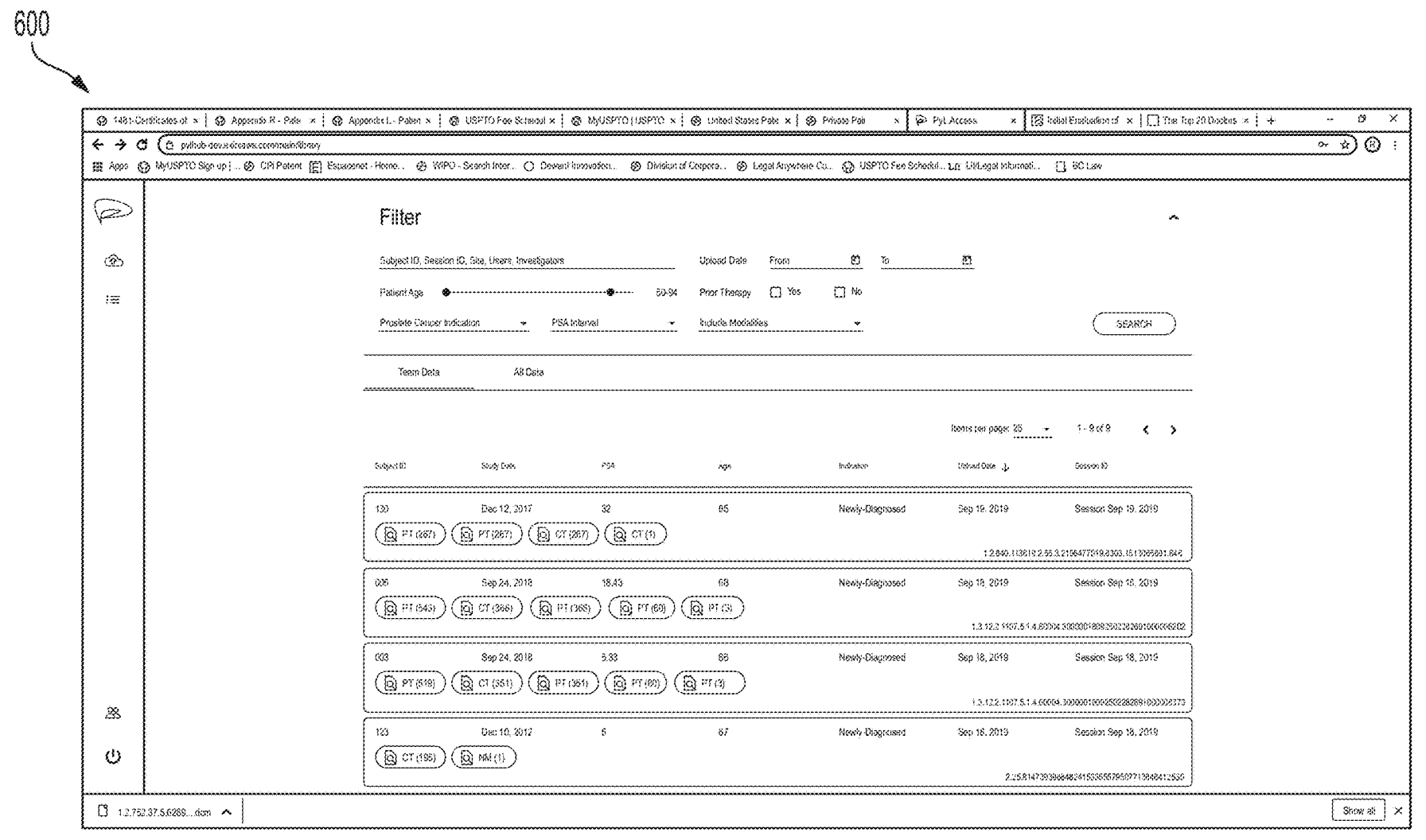
Figure 6B:
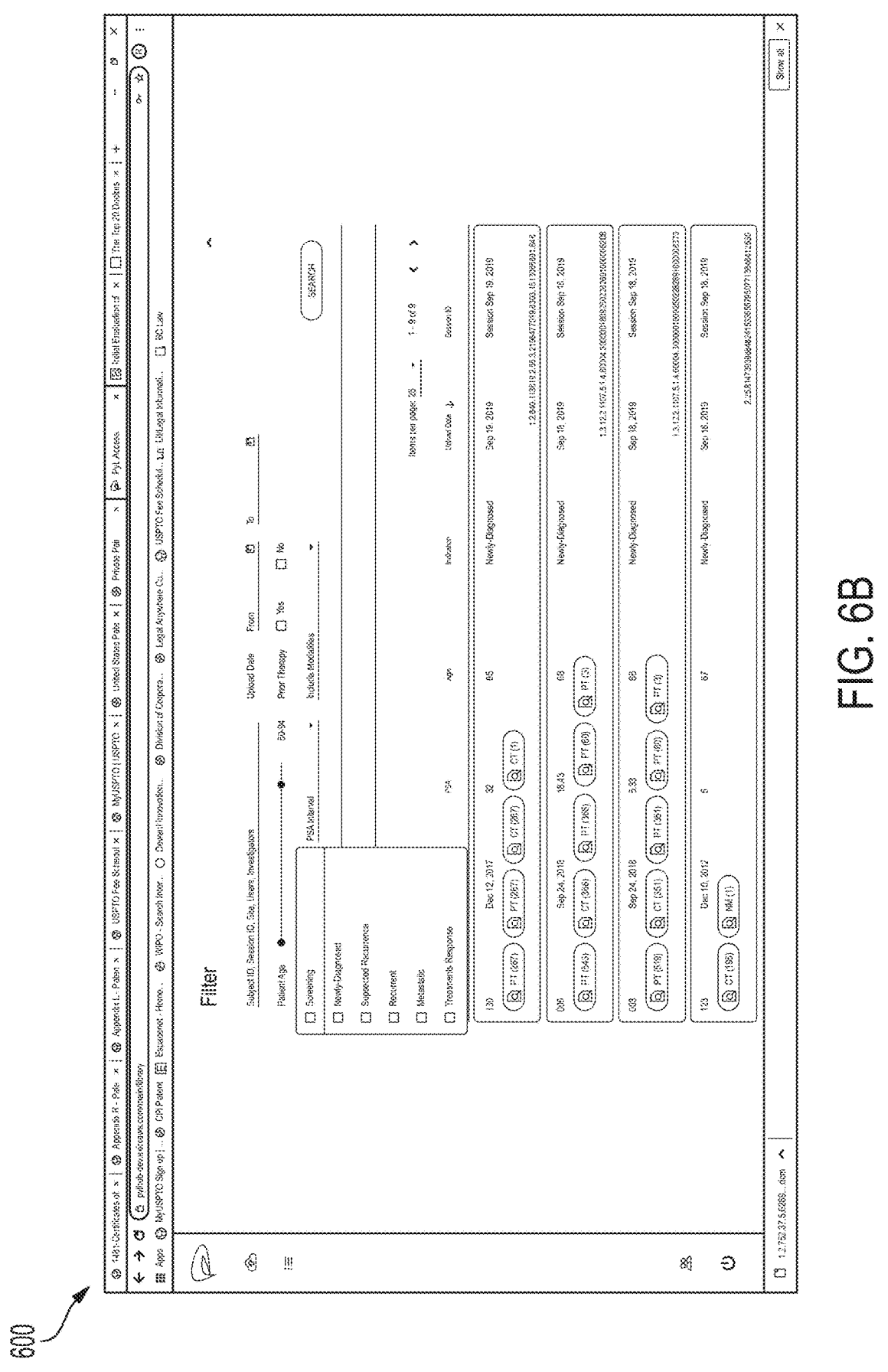
Figure 6C:
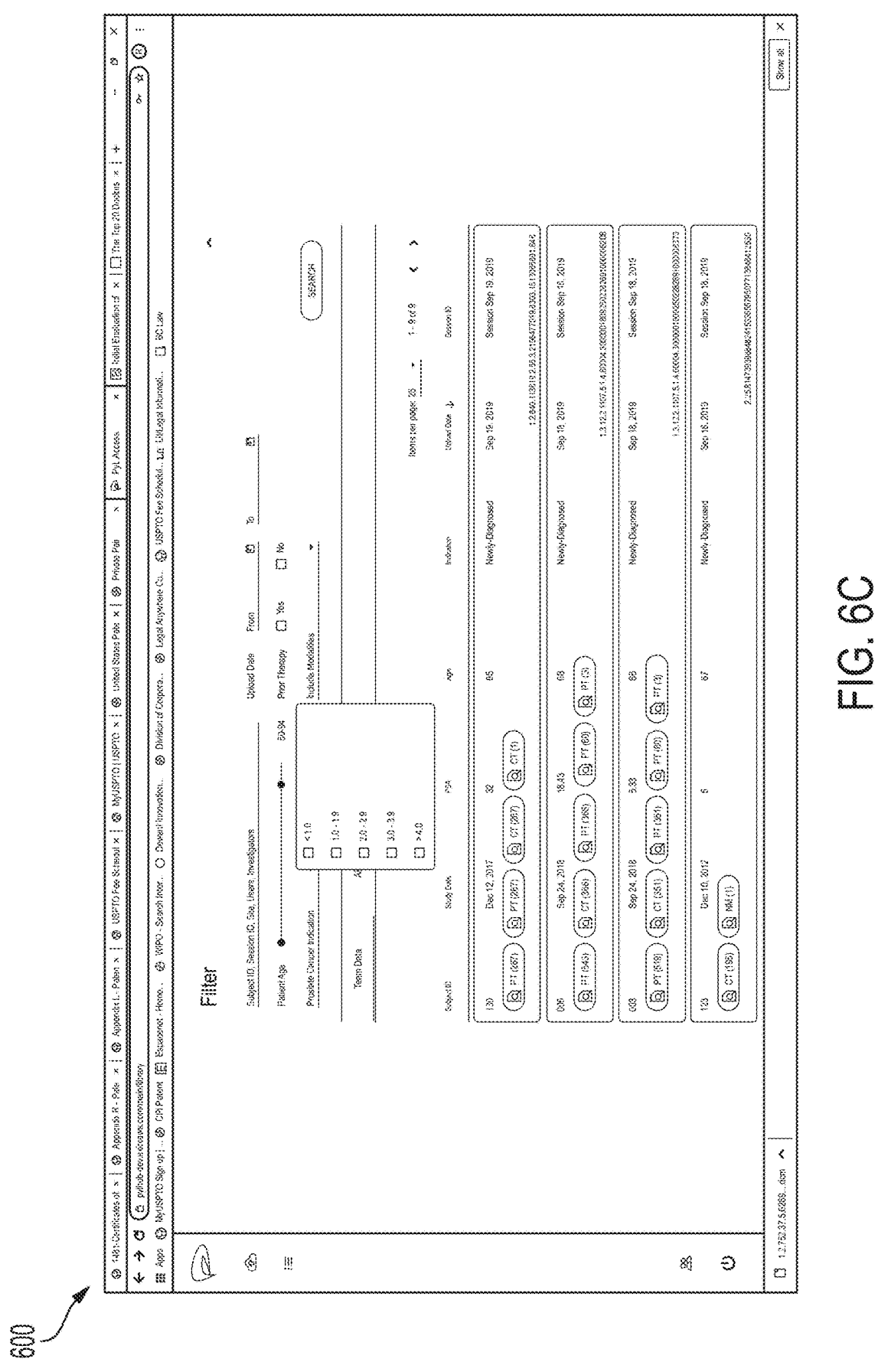
Figure 6D:
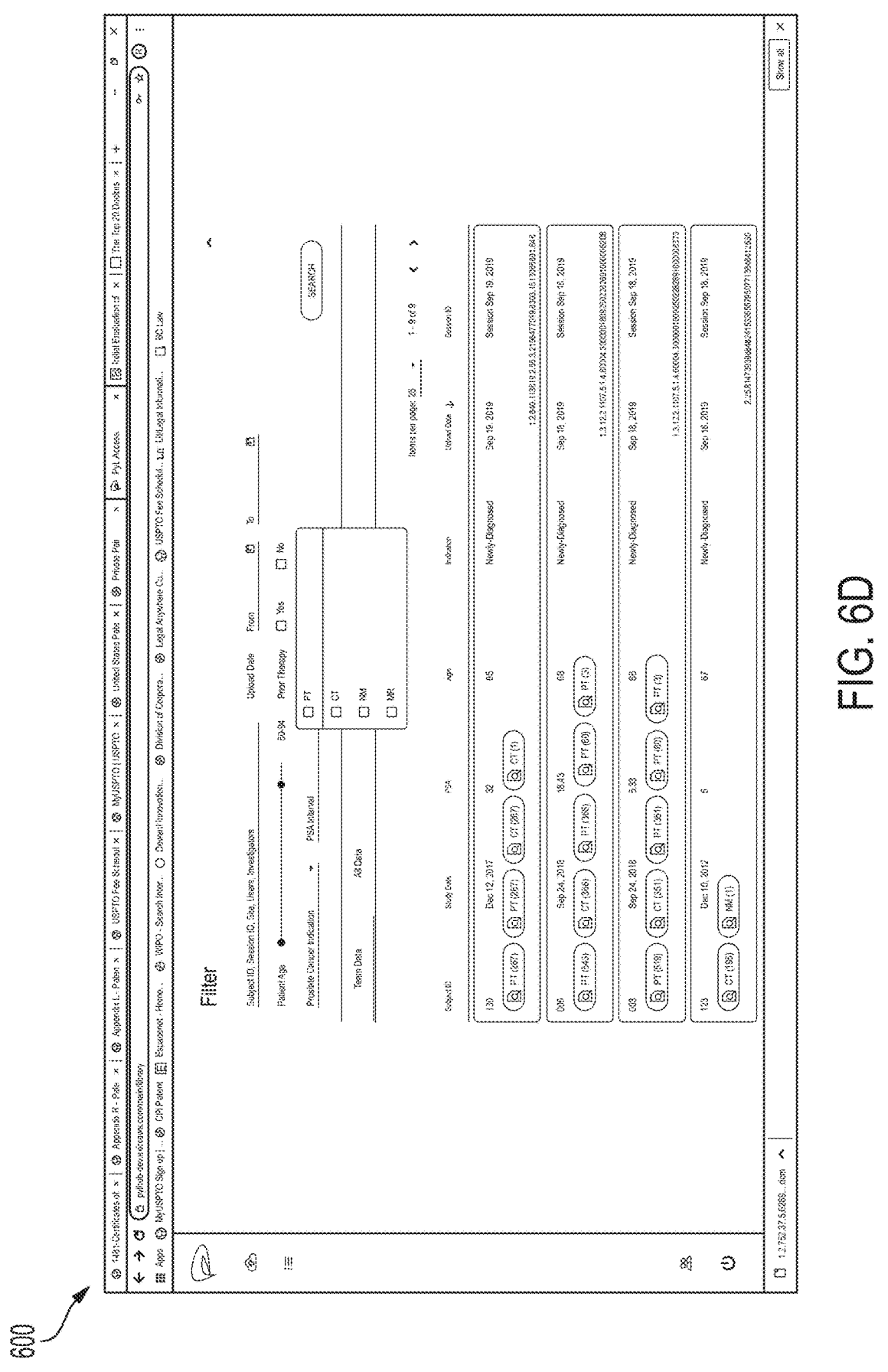

FIG. 6A is another screenshot of the GUI shown in FIG. 1A, showing a view that allows a user to inspect uploaded medical image data;

FIG. 6B is another screenshot of the GUI view shown in FIG. 6A, according to an illustrative embodiment;

FIG. 6C is another screenshot of the GUI view shown in FIG. 6A, according to an illustrative embodiment;

FIG. 6D is another screenshot of the GUI view shown in FIG. 6A, according to an illustrative embodiment;

FIG. 7A is a screenshot of a GUI, showing a view that allows a user to inspect uploaded medical image data;

Figure 1A:
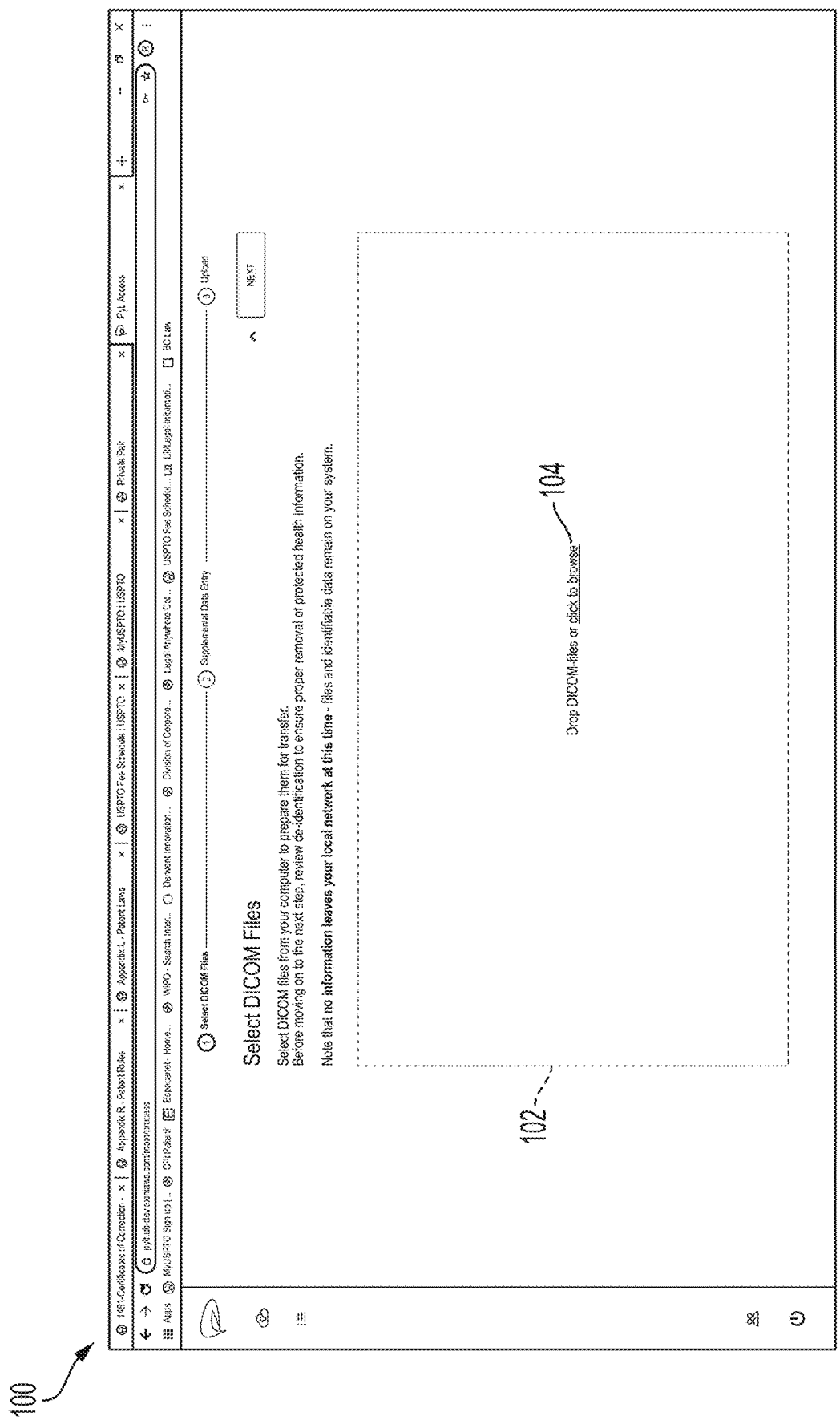
FIG. 1A is a screenshot of a graphical user interface (GUI) for allowing a user to upload files comprising medical images to a cloud-based platform, according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

Definitions

Administering: As used herein, "administering" an agent means introducing a substance (e.g., an imaging agent) into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments.

Image: As used herein, the term "image", for example, as in a three-dimensional image of a patient, includes any visual representation, such as a photo, a video frame, streaming video, as well as any electronic, digital, or mathematical analogue of a photo, video frame, or streaming video. Any apparatus described herein, in certain embodiments, includes a display for displaying an image or any other result produced by a processor. Any method described herein, in certain embodiments, includes a step of displaying an image or any other result produced by the method.

Radionuclide: As used herein, "radionuclide" refers to a moiety comprising a radioactive isotope of at least one element. Exemplary suitable radionuclides include but are not limited to those described herein. In some embodiments, a radionuclide is one used in positron emission tomography (PET). In some embodiments, a radionuclide is one used in single-photon emission computed tomography (SPECT). In some embodiments, a non-limiting list of radionuclides includes $^{99m}Tc$, $^{111}In$, $^{64}Cu$, $^{67}Ga$, $^{68}Ga$, $^{188}Re$, $^{153}Sm$, $^{177}Lu$, $^{67}Cu$, $^{123}I$, $^{124}I$, $^{125}I$, $^{126}I$, $^{131}I$, $^{11}C$, $^{13}N$, $^{15}O$, $^{18}F$, $^{153}Sm$, $^{166}Ho$, $^{177}Lu$, $^{149}Pm$, $^{90}Y$, $^{213}Bi$, $^{103}Pd$, $^{109}Pd$, $^{159}Gd$, $^{140}La$, $^{198}Au$, $^{199}Au$, $^{199}Yb$, $^{175}Yb$, $^{165}Yb$, $^{166}Dy$, $^{105}Rh$, $^{111}Ag$, $^{89}Zr$, $^{225}AC$, $^{82}Rb$, $^{75}Br$, $^{76}Br$, $^{77}Br$, $^{80}Br$, $^{80m}Br$, $^{82}Br$, $^{83}Br$, $^{211}At$ and $^{192}Ir$.

Radiopharmaceutical: As used herein, the term "radiopharmaceutical" refers to a compound comprising a radionuclide. In certain embodiments, radiopharmaceuticals are used for diagnostic and/or therapeutic purposes. In certain embodiments, radiopharmaceuticals include small molecules that are labeled with one or more radionuclide(s), antibodies that are labeled with one or more radionuclide(s), and antigen-binding portions of antibodies that are labeled with one or more radionuclide(s).

3D, three-dimensional: As used herein, "3D" or "three-dimensional" with reference to an "image" means conveying information about three spatial dimensions. A 3D image may be rendered as a dataset in three dimensions and/or may be displayed as a set of two-dimensional representations, or as a three-dimensional representation. In certain embodiments, a 3-D image is represented as voxel (e.g., volumetric pixel) data.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader—the presence and/or placement of a header is not intended to limit the scope of the subject matter described herein.

A. Secure Upload of Medical Images

Described herein are systems and methods that provide for secure upload of files comprising medical images and associated metadata from a local computing device to a network-based platform.

Storing and analyzing medical images using cloud-based platforms is attractive, since cloud-based platforms offer significant advantages over keeping files on local computing devices. Cloud-based systems facilitate communication between and allow data to be readily accessed by different sites, such different hospitals, clinics, and research facilities.

Moreover, they offer the ability to shift the burden of maintaining a complex computing network to a third party, allowing facilities to dedicate resources to activities more in line with their primary purpose, such as providing medical care and/or carrying out research. At the same time, cloud-based platforms often provide significant improvements in computing capabilities.

For example, a cloud based platform can serve as a repository for medical images collected for multiple patients over the course years of care, involving, for example, disease diagnosis, and treatment monitoring, or during clinical trials. Moreover, such platforms may serve as a hub, not only providing for storage and/or accessing of medical images, but also providing tools for computer aided image analysis. For example, PCT Appl. PCT/US17/58418, filed Oct. 26, 2017 (publication no. WO/2018/081354), the content of which is incorporated herein by reference in its entirety, provides examples of cloud-based image analysis platforms that allow a user to upload images, access them, and analyze them using various tools, suited for different imaging modalities. For example, once images are uploaded, bone-scan image analysis tools, such as aBSI (automated bone scan index), can be used to evaluate disease burden and identify metastases from scintigraphy images. Other image analysis tools, suited for analyzing three dimensional images such as SPECT/CT and PET/CT composite images For example, PCT Applications PCT/US19/12486, filed Jan. 7, 2019 (publication no. WO/2019/136349) and PCT/EP2020/050132, filed Jan. 6, 2020 (publication no. WO/2020/144134), the content of each of which are hereby incorporated by reference in their entirety, describe 3D image segmentation techniques and processing approaches that can be used to evaluate uptake of various radiopharmaceuticals in specific organs of interest and/or identify hotspots in functional images (e.g., PET, SPECT images) that represent cancerous lesions. Accordingly, utilizing such cloud-based platforms streamlines image storage and analysis, and facilitates access to valuable analysis tools.

Despite the advantages of cloud based platforms, security of private medical data is an important concern. The ability to ensure that sensitive private data, such as information that could be used to ascertain the identify of a particular patient to which various records belong, is kept private, and not transmitted to other parties is an important requirement for use of data-sharing and cloud-based systems. In many cases, for example particularly where data is shared and/or used for research purposes, sensitive data can and must be removed to ensure that any medical data cannot identified as belonging to a particular individual (e.g., patient).

Ensuring adherence to such privacy controls is non-trivial, and approaches that facilitate maintaining data privacy and allow users to interact with cloud-based systems confidently are highly desirable. Accordingly, in certain embodiments, the systems and methods described herein allow a user to upload files comprising medical images to a cloud-based image analysis platform while maintaining appropriate privacy controls by de-identifying portions of metadata associated with medical images prior to upload. In particular, approaches described herein prevent the network-based platform from accessing sensitive data as it is prepared for upload. Prior to file upload, sensitive elements are identified and flagged and their values removed and/or masked. Notably, in certain embodiments, the approaches described herein provide for graphical user interfaces (GUIs) that allow a user to visually inspect and control the de-identification of metadata prior to upload in an intuitive manner.

Processing performed to display the GUI elements, view data prior to upload, and de-identify data by identifying and removing and/or masking values of flagged data elements are performed by a processor of a local computing device that is not part of the network-based platform to which files are uploaded. In certain embodiments, the local computing device is in communication with an imaging system [e.g., a computed tomography (CT) scanner; e.g., a magnetic resonance imaging (MRI) scanner; e.g., a positron emission tomography (PET) scanner; e.g., a single photon emission computed tomography (SPECT) scanner; e.g., a gamma camera scanner (e.g., a scintigraphy imaging scanner); e.g., a combined CT/PET, CT/SPECT, MRI/PET, MRI/SPECT scanner]. In certain embodiments, the local computing device on a local network (e.g., a private, limited access network, such as a network of a hospital or group of hospitals, a network of a research organization, and the like) that is not part of the network-based (e.g., a cloud-based) analysis and/or decision support platform.

As described herein, in certain embodiments the systems and methods described herein provide for analysis and secure upload of nuclear medicine images. Nuclear medicine images are obtained using a nuclear imaging modality such as bone scan imaging, Positron Emission Tomography (PET) imaging, and Single-Photon Emission Tomography (SPECT) imaging.

In certain embodiments, nuclear medicine images use imaging agents comprising radiopharmaceuticals. Nuclear medicine images are obtained following administration of a radiopharmaceutical to a patient (e.g., a human subject), and provide information regarding the distribution of the radiopharmaceutical within the patient. Radiopharmaceuticals are compounds that comprise a radionuclide.

Nuclear medicine images (e.g., PET scans; e.g., SPECT scans; e.g., whole-body bone scans; e.g. composite PET-CT images; e.g., composite SPECT-CT images) detect radiation emitted from the radionuclides of radiopharmaceuticals to form an image. The distribution of a particular radiopharmaceutical within a patient may be determined by biological mechanisms such as blood flow or perfusion, as well as by specific enzymatic or receptor binding interactions. Different radiopharmaceuticals may be designed to take advantage of different biological mechanisms and/or particular specific enzymatic or receptor binding interactions and thus, when administered to a patient, selectively concentrate within particular types of tissue and/or regions within the patient. Greater amounts of radiation are emitted from regions within the patient that have higher concentrations of radiopharmaceutical than other regions, such that these regions appear brighter in nuclear medicine images. Accordingly, intensity variations within a nuclear medicine image can be used to map the distribution of radiopharmaceutical within the patient. This mapped distribution of radiopharmaceutical within the patient can be used to, for example, infer the presence of cancerous tissue within various regions of the patient's body.

For example, upon administration to a patient, technetium 99 m methylenediphosphonate ($^{99m}$Tc MDP) selectively accumulates within the skeletal region of the patient, in particular at sites with abnormal osteogenesis associated with malignant bone lesions. The selective concentration of radiopharmaceutical at these sites produces identifiable hotspots—localized regions of high intensity in nuclear medicine images. Accordingly, presence of malignant bone lesions associated with metastatic prostate cancer can be inferred by identifying such hotspots within a whole-body scan of the patient. As described in the following, risk indices that correlate with patient overall survival and other prognostic metrics indicative of disease state, progression, treatment efficacy, and the like, can be computed based on automated analysis of intensity variations in whole-body scans obtained following administration of $^{99m}$Tc MDP to a patient. In certain embodiments, other radiopharmaceuticals can also be used in a similar fashion to $^{99m}$Tc MDP.

In certain embodiments, the particular radiopharmaceutical used depends on the particular nuclear medicine imaging modality used. For example 18 F sodium fluoride (NaF) also accumulates in bone lesions, similar to $^{99m}$Tc MDP, but can be used with PET imaging. In certain embodiments, PET imaging may also utilize a radioactive form of the vitamin choline, which is readily absorbed by prostate cancer cells.

In certain embodiments, radiopharmaceuticals that selectively bind to particular proteins or receptors of interest—particularly those whose expression is increased in cancerous tissue may be used. Such proteins or receptors of interest include, but are not limited to tumor antigens, such as CEA, which is expressed in colorectal carcinomas, Her2/neu, which is expressed in multiple cancers, BRCA 1 and BRCA 2, expressed in breast and ovarian cancers; and TRP-1 and -2, expressed in melanoma.

For example, human prostate-specific membrane antigen (PSMA) is upregulated in prostate cancer, including metastatic disease. PSMA is expressed by virtually all prostate cancers and its expression is further increased in poorly differentiated, metastatic and hormone refractory carcinomas. Accordingly, radiopharmaceuticals corresponding to PSMA binding agents (e.g., compounds that a high affinity to PSMA) labelled with one or more radionuclide(s) can be used to obtain nuclear medicine images of a patient from which the presence and/or state of prostate cancer within a variety of regions (e.g., including, but not limited to skeletal regions) of the patient can be assessed. In certain embodiments, nuclear medicine images obtained using PSMA binding agents are used to identify the presence of cancerous tissue within the prostate, when the disease is in a localized state. In certain embodiments, nuclear medicine images obtained using radiopharmaceuticals comprising PSMA binding agents are used to identify the presence of cancerous tissue within a variety of regions that include not only the prostate, but also other organs and tissue regions such as lungs, lymph nodes, and bones, as is relevant when the disease is metastatic.

In particular, upon administration to a patient, radionuclide labelled PSMA binding agents selectively accumulate within cancerous tissue, based on their affinity to PSMA. In a similar manner to that described above with regard to $^{99m}$Tc MDP, the selective concentration of radionuclide labelled PSMA binding agents at particular sites within the patient produces detectable hotspots in nuclear medicine images. As PSMA binding agents concentrate within a variety of cancerous tissues and regions of the body expressing PSMA, localized cancer within a prostate of the patient and/or metastatic cancer in various regions of the patient's body can be detected, and evaluated. Risk indices that correlate with patient overall survival and other prognostic metrics indicative of disease state, progression, treatment efficacy, and the like, can be computed based on automated analysis of intensity variations in nuclear medicine images obtained following administration of a PSMA binding agent radiopharmaceutical to a patient.

A variety of radionuclide labelled PSMA binding agents may be used as radiopharmaceutical imaging agents for nuclear medicine imaging to detect and evaluate prostate cancer. In certain embodiments, the particular radionuclide labelled PSMA binding agent that is used depends on factors such as the particular imaging modality (e.g., PET; e.g., SPECT) and the particular regions (e.g., organs) of the patient to be imaged. For example, certain radionuclide labelled PSMA binding agents are suited for PET imaging, while others are suited for SPECT imaging. For example, certain radionuclide labelled PSMA binding agents facilitate imaging a prostate of the patient, and are used primarily when the disease is localized, while others facilitate imaging organs and regions throughout the patient's body, and are useful for evaluating metastatic prostate cancer.

A variety of PSMA binding agents and radionuclide labelled versions thereof are described in U.S. Pat. Nos. 8,778,305, 8,211,401, and 8,962,799, each of which are incorporated herein by reference in their entireties. Several PSMA binding agents and radionuclide labelled versions thereof are also described in PCT Application PCT/US2017/058418, filed Oct. 26, 2017 (PCT publication WO 2018/081354), the content of which is incorporated herein by reference in its entirety.

A. i. Selection and Pre-Processing of Files

Figure 1B:
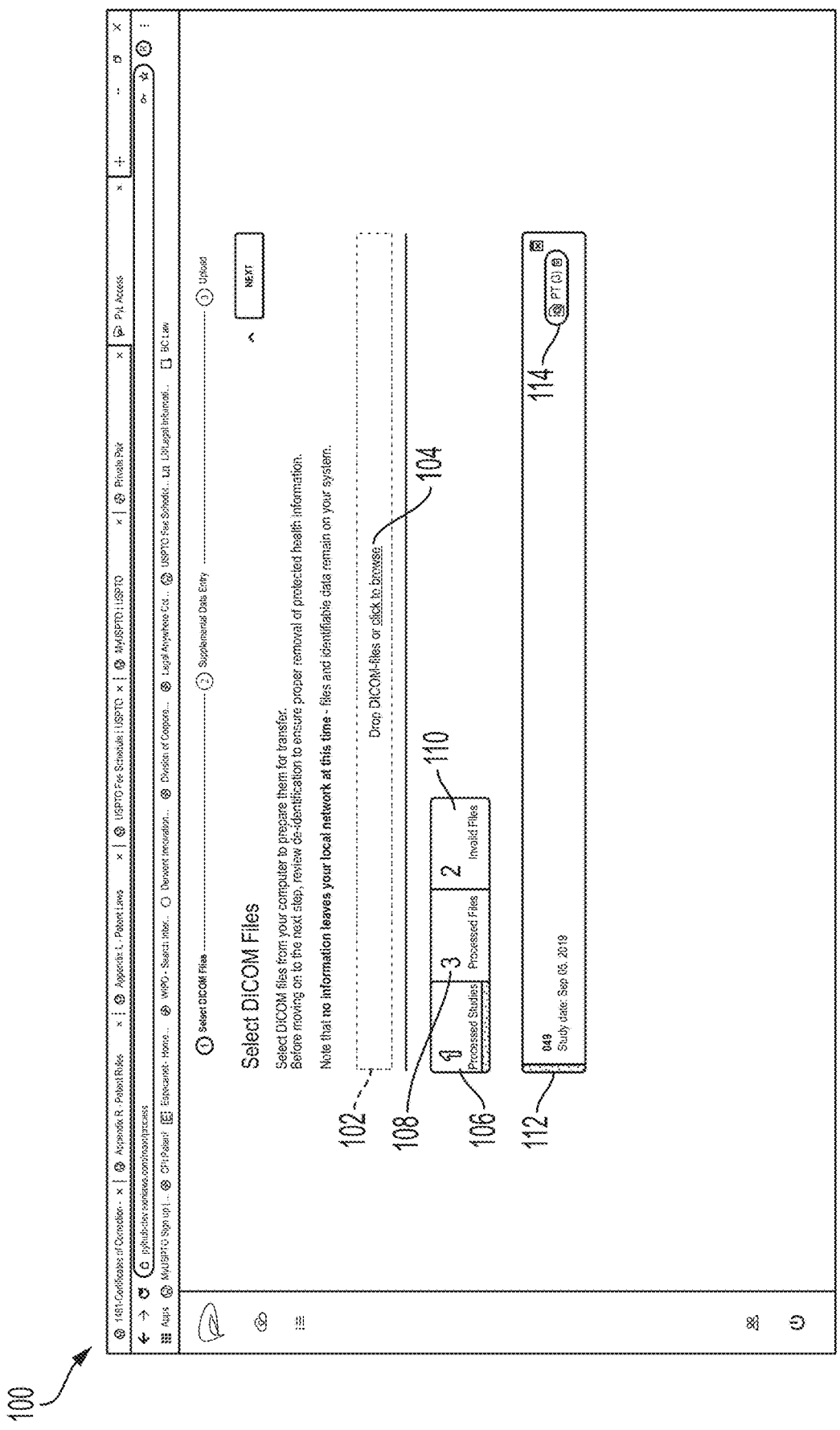
FIG. 1B is another screenshot of the GUI shown in FIG. 1A, showing a view that appears after a user has selected files for upload, according to an illustrative embodiment.

For example, FIG. 1A shows a screenshot of an initial view of a GUI 100 that allows a user to select, review, and upload files comprising medical images and associated metadata. As shown in FIG. 1A, a user may select files via an intuitive 'drag-and-drop' approach (e.g., by dragging files on their local computing device into window 102), or click link 104 to browse for files via a traditional file explorer. Following user selection of files to upload, the user selected files are pre-processed and validated. In certain embodiments, files corresponding to a same study are grouped together. For example, as shown in FIG. 1B, multiple processed files may be grouped together into a single study. As shown in the GUI view of FIG. 1B, selectable graphical control elements may be displayed in order to allow a user to inspect processed studies, individual files, as well as files determined to be invalid during the preprocessing step. In the view shown in FIG. 1B, the Processed Studies selectable element 106 is selected and a listing of processed studies is shown below. Only a single study is shown in FIG. 1B, but multiple studies may be shown as well. Icon 112 represents the processed study, and includes a selectable icon 114 representing a set of files corresponding to the study. Icon 114 indicates a particular type of image—a PET image, and shows the number "(3)", indicating the three files comprising PET image data processed.

Figure 1C:
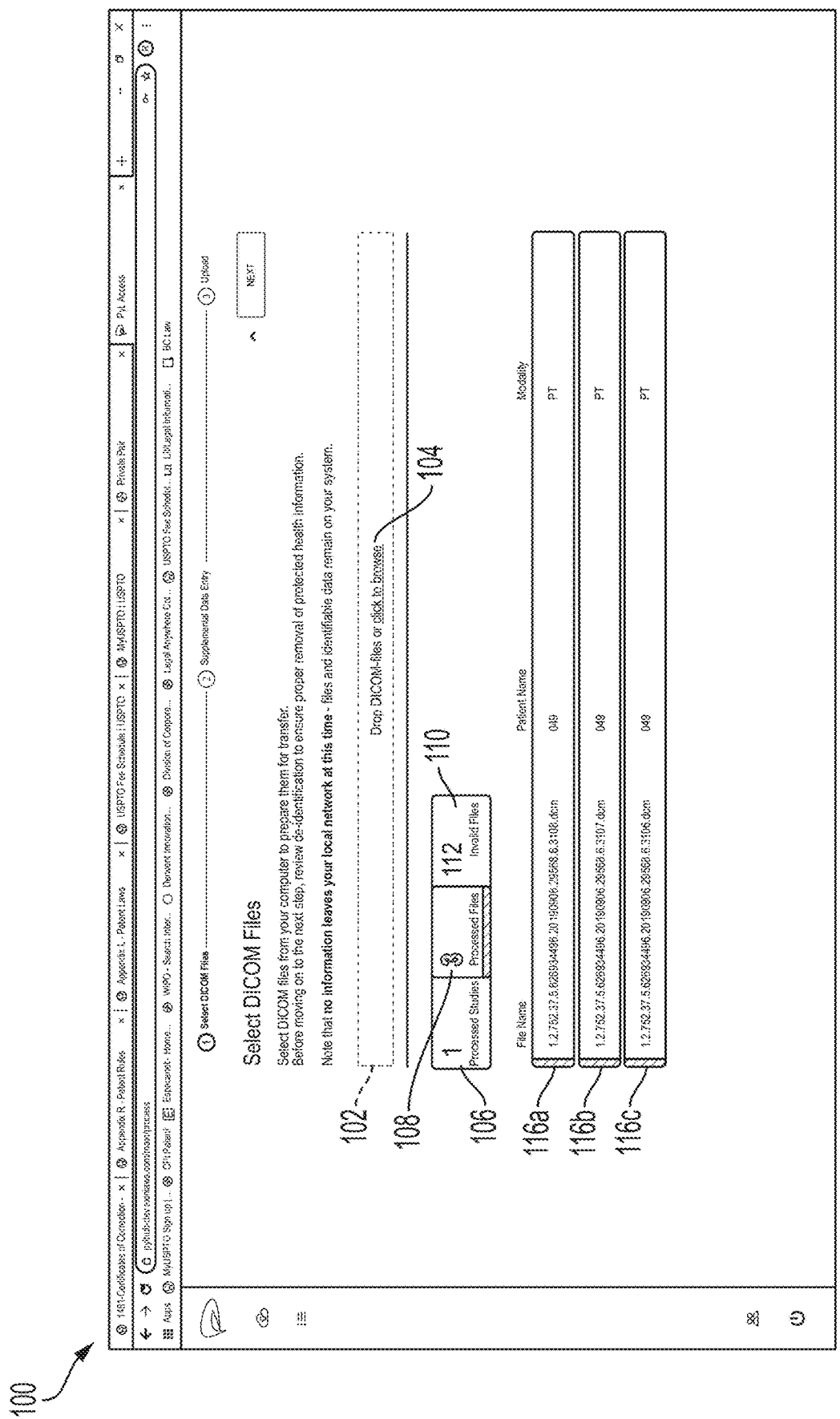
FIG. 1C is another screenshot of the GUI shown in FIG. 1A, showing another view that appears after a user has selected files for upload, according to an illustrative embodiment.

As shown in FIG. 1C, following a user selection of selectable element 108 causes display of a listing of individual processed files, with each processed file represented by an icon 116a, 116b, and 116c. The icons 116a, 116b, and 116c show information about the processed files, such as the filename, a patient name, and an indication of the imaging modality used to obtain the medical image of the file.

Figure 1D:
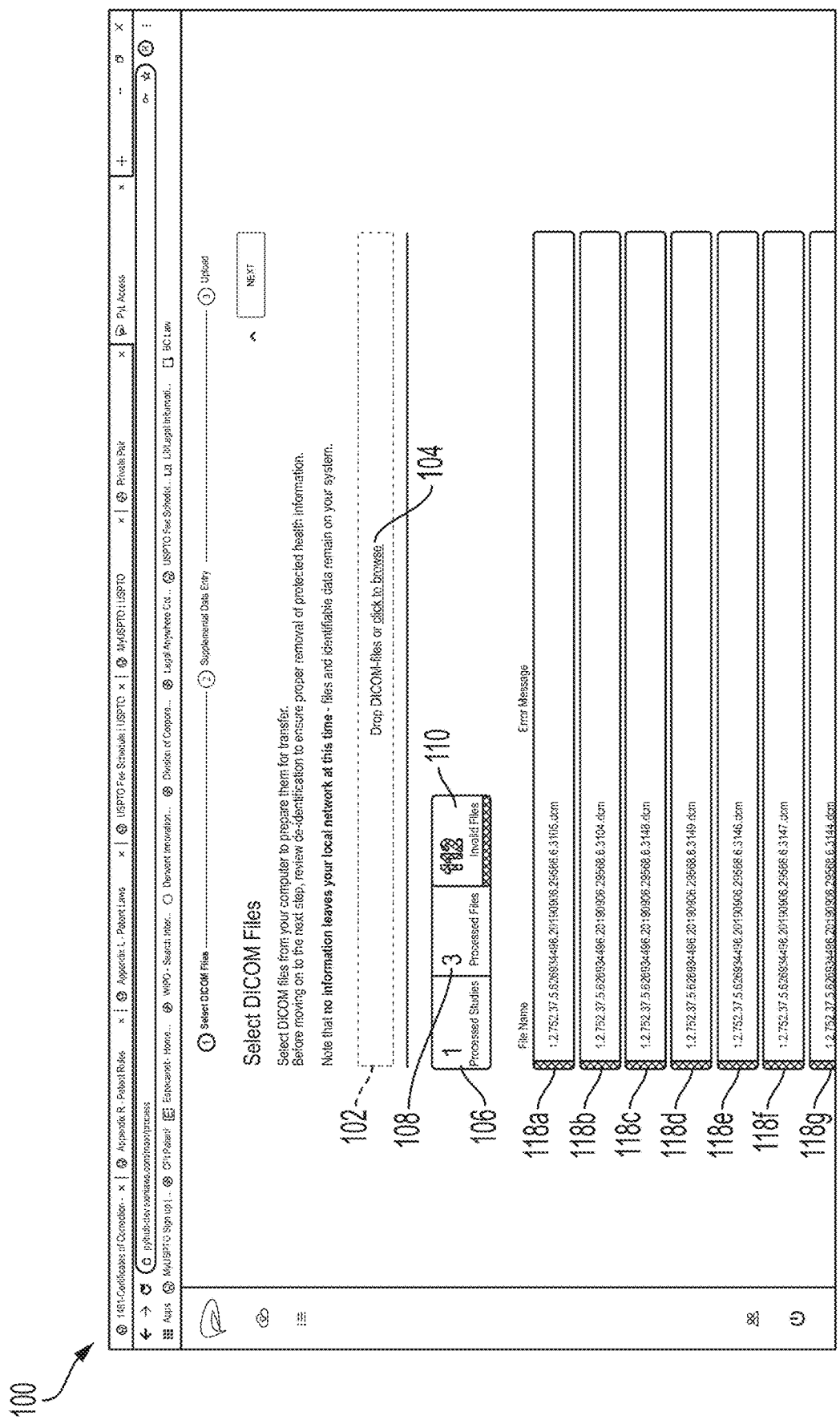
FIG. 1D is another screenshot of the GUI shown in FIG. 1A, showing another view that appears after a user has selected files for upload, according to an illustrative embodiment.

FIG. 1D shows a view that appears upon a user selection of selectable element 110 to display files identified as invalid during preprocessing. As shown in FIG. 1D, each invalid file is identified by an icon—e.g., icons 118a, 118b, 118c, 118d, 118e, 118f, and 118g.

Figure 1E:
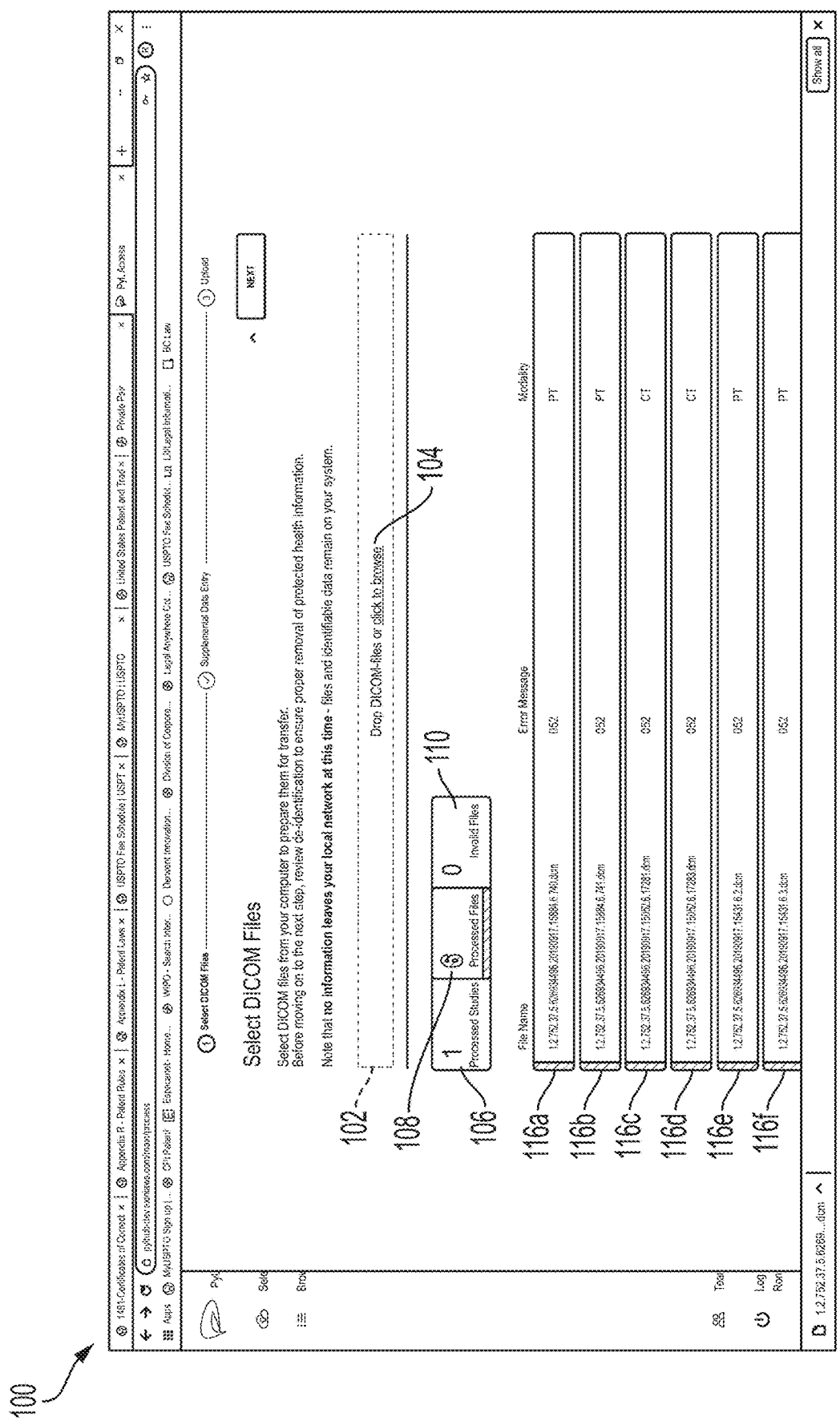
FIG. 1E is another screenshot of the GUI shown in FIG. 1A, showing another view that appears after a user has selected files for upload, according to an illustrative embodiment.

FIG. 1E shows another view of the GUI, similar to FIG. 1C, in which all files were successfully processed, and no files were found invalid. Icons 116a, 116b, 116c, 116d, 116e, and 116f represent the different processed files. As shown in FIG. 1E, medical images obtained using different modalities are selected. In particular, files represented by icons 116a, 116b, 116e, and 116f comprise medical images obtained via PET imaging (e.g., they are labeled with the identifier "PT") and files represented by icons 116c and 116d comprise medical images obtained using CT imaging (e.g., they are labeled with the identifier "CT").

A. ii. Review of Medical Images and Associated Metadata

Figure 2A:
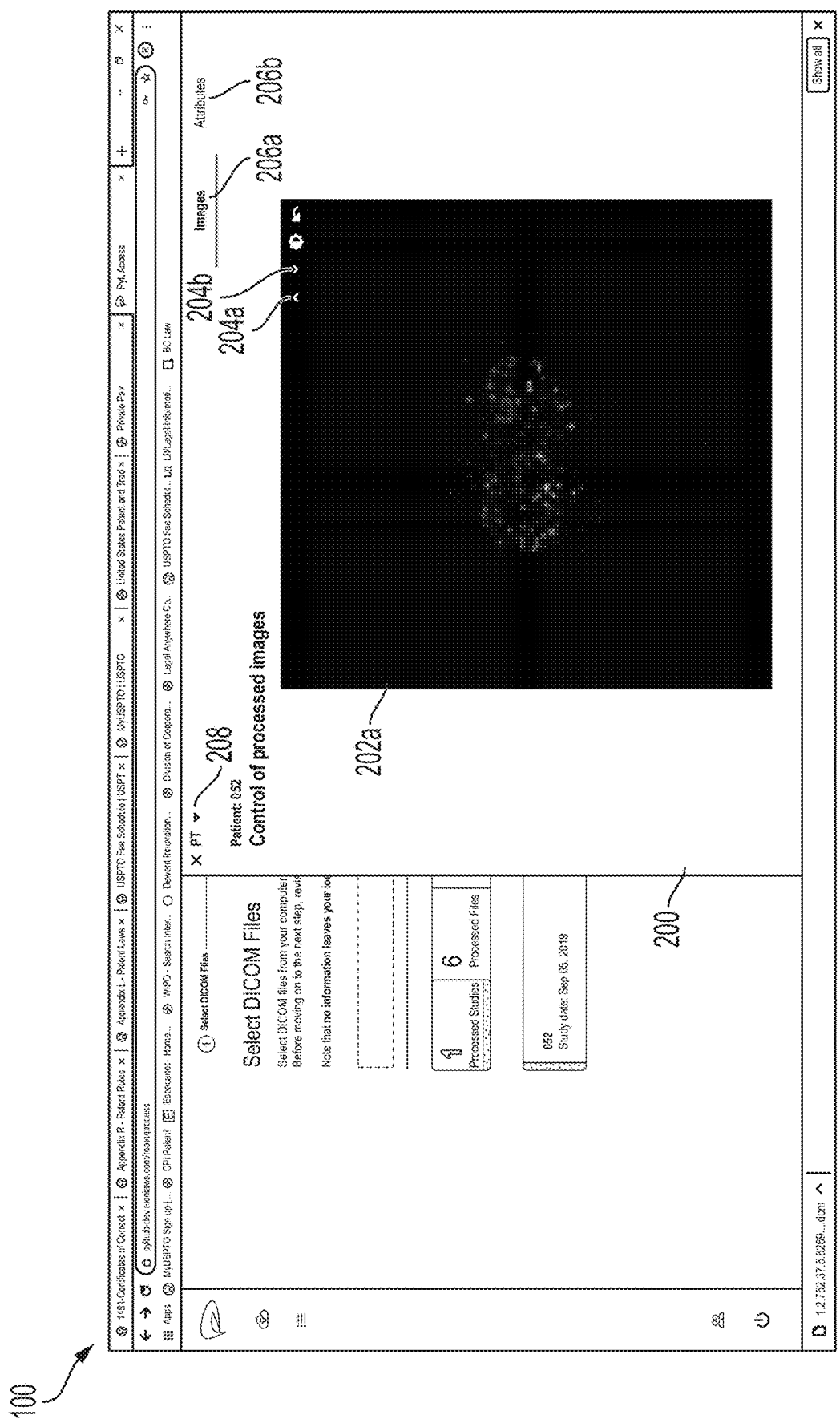
FIG. 2A is another screenshot of the GUI shown in FIG. 1A, showing a view of a pop-up window that allows a user to review a specific medical image and its associated metadata, according to an illustrative embodiment.
Figure 2B:
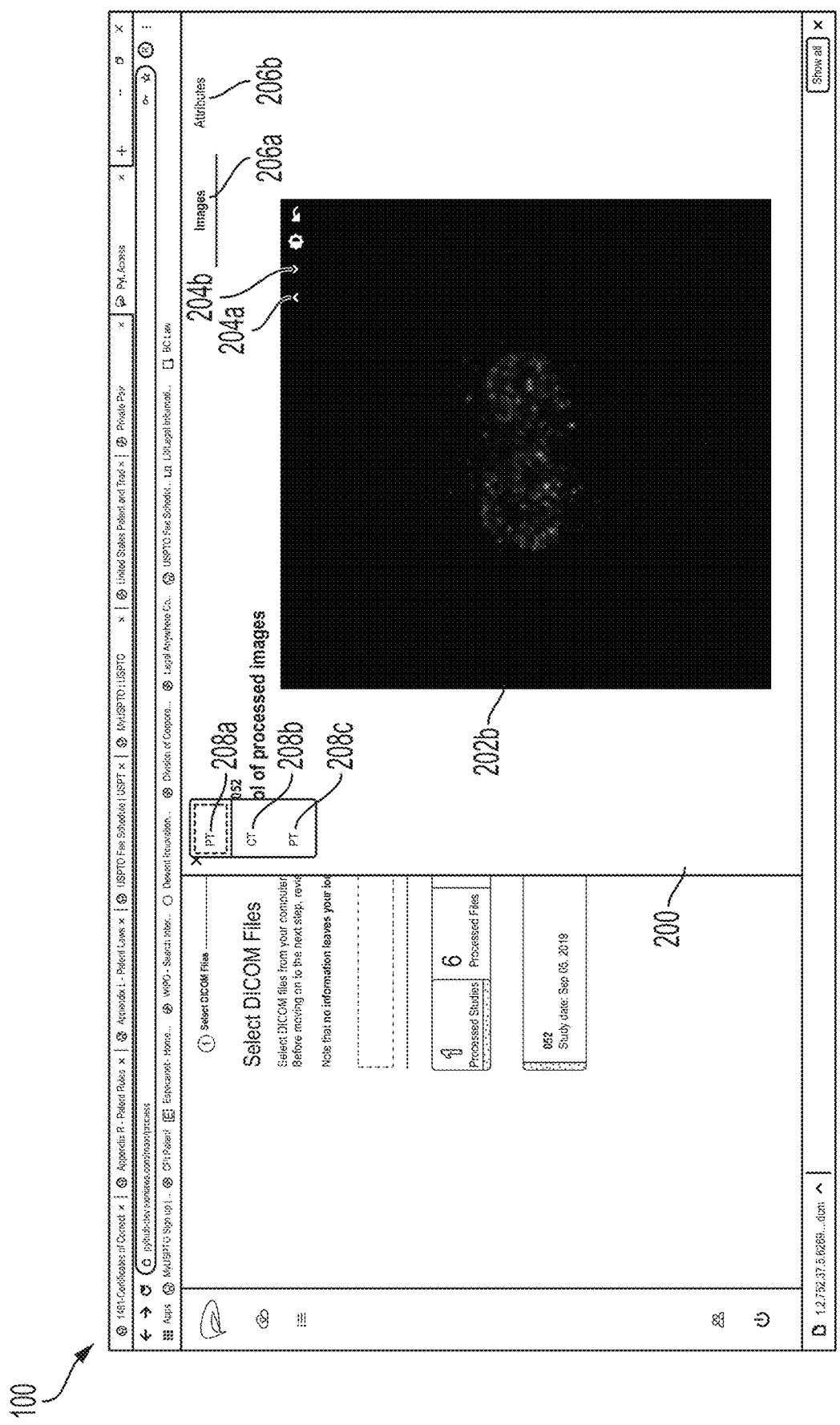
FIG. 2B is another screenshot of the GUI shown in FIG. 1A, showing another view of the pop-up window that allows a user to review a specific medical image and its associated metadata, according to an illustrative embodiment.
Figure 2C:
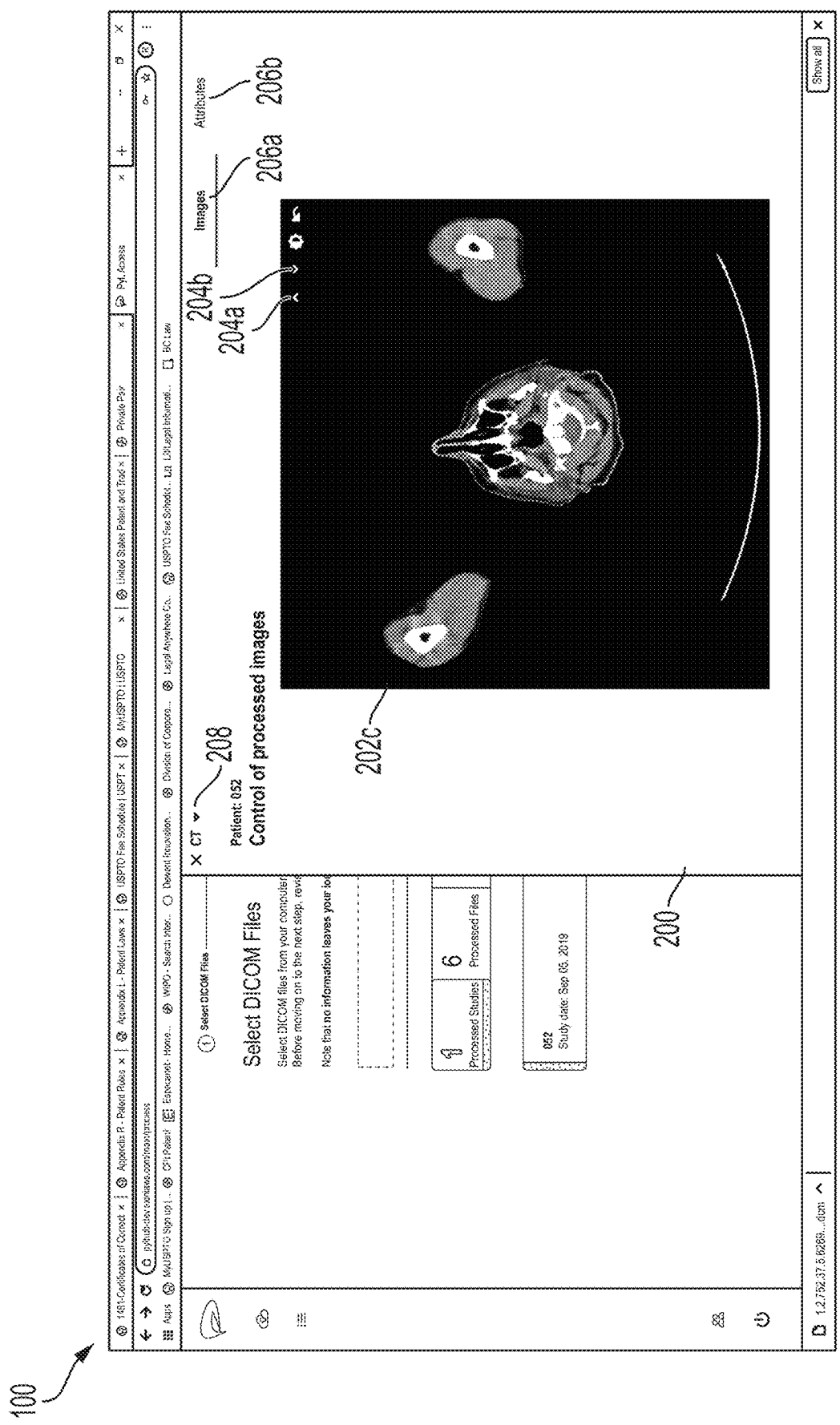
FIG. 2C is another screenshot of the GUI shown in FIG. 1A, showing another view of the pop-up window that allows a user to review a specific medical image and its associated metadata, according to an illustrative embodiment.

In certain embodiments, a user can click icon 114 (shown in FIG. 1B) to review files comprising the medical images. As shown in FIG. 2A, following the user click on icon 114, window 200 is displayed (e.g., as an overlay, as shown in FIG. 2A, or in other manners, e.g., as a separate window, in a separate browser tab, etc.), allowing the user to review medical images and associated metadata within the files. Window 200 includes an initial display of a first medical image 202a of a first set of medical images. Window 200 also includes graphical control elements 204a, 204b, for scrolling through different images in a set of multiple related images. For example, a user click may click on element 204b to move to a next image in a set, bringing up image 202b shown in FIG. 2B. A user may also click element 208 to view other sets of medical images, for example to view images collected using a different imaging modality. For example, upon selecting the second element 208b of the popup shown in FIG. 2B that appears when a user clicks on element 208, a CT image 202c is shown. Other sets of images can be viewed by clicking other elements of the popup, e.g., 208a, 208c for different sets of PET images.

A user may also click on text "Attributes" 206b to view associated metadata to review de-identification. Upon the user selection to review de-identification, a graphical representation 210 of associated metadata of a particular file is displayed. The associated metadata includes various individual data elements, which are displayed in a tabular fashion. A user may scroll through the table to view different data elements as shown in FIG. 3A and FIG. 3B.

Three different views of associated metadata are available. A user may select between the different views via control elements (e.g., radio buttons) 212a, 212b, and 212c.

One view, "changes" conveys changes made or that will be made to the associated metadata in order to remove and/or mask values of certain sensitive data elements that convey information that could be used to identify a particular patient. Prior to upload, such sensitive data elements are identified in the associate metadata in each file, and flagged for de-identification. For each flagged data element, the value of that element is either removed or replaced with a masking value that obscures and/or convey more limited information than the value itself. Certain flagged elements may be removed entirely, while others may be masked. The particular protocol listing which elements to flag, and in turn, which flagged elements are to be removed and which are to be masked, may be stored in an accessible protocol file (e.g., on the local computing device).

Figure 3A:
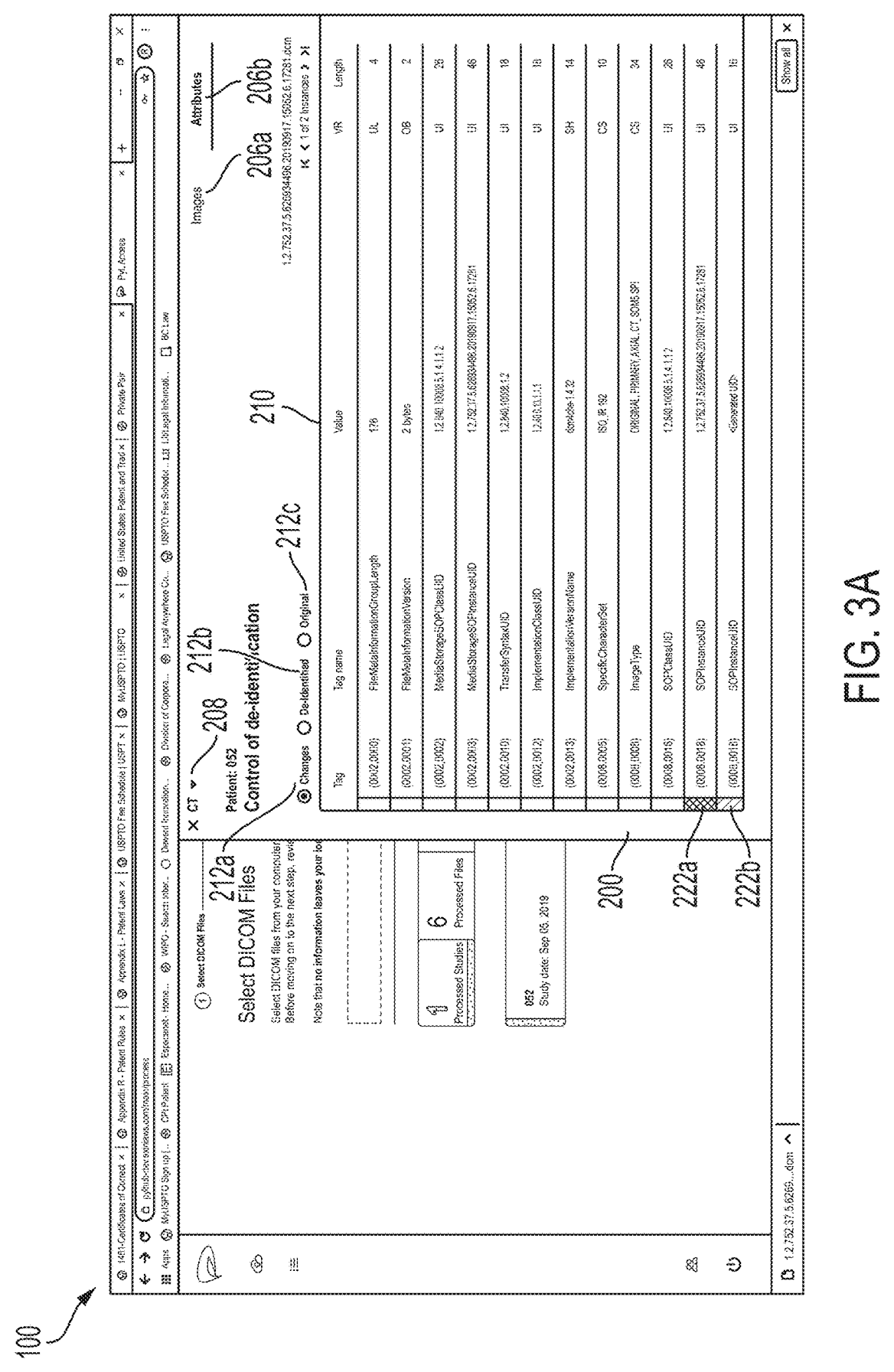
Figure 3B:
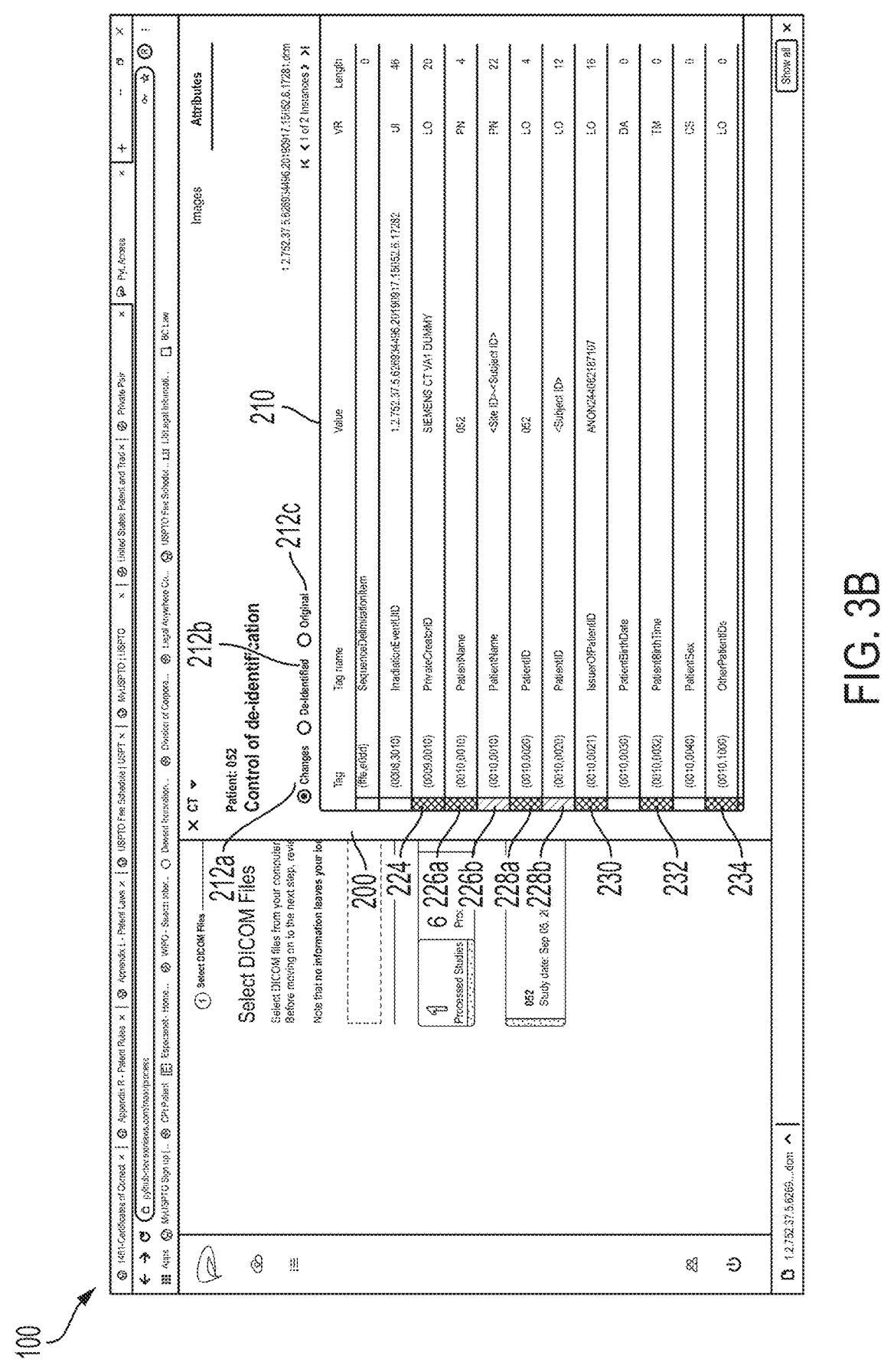

As shown in FIG. 3A and FIG. 3B, flagged data elements are visually indicated via a colored bar. Various other approaches for visually identifying and displaying flagged data elements are also possible. For example, other colorization schemes can be used, entire rows of the table could be highlighted, different fonts or colors of text used, other icons (e.g., as opposed to colored bars) used. Red colored bars indicate elements to be removed, while green bars signify additions—namely, masking values replacing the original initial value of certain particular data elements. Accordingly, data elements to be masked are observable as pairs of like named elements identified by a red and then, below, a green, bar. For example, in FIG. 3A rows 222a and 222b show that a value of the data element named "SOPInstanceUID" is removed and replaced with masking value. Similarly, rows 226a and 226b show that the data element called "PatientName" is masked, and rows 228a and 228b show that the data element called "PatientID" is masked. Rows 224, 230, 232, and 234, flagged in red without a corresponding added entry beneath signify data elements that are removed entirely. Accordingly, this intuitive graphical display of metadata changes informs the user of how the data that they upload will be de-identified, and allows them to ensure appropriate privacy controls are taken.

Figure 3C:
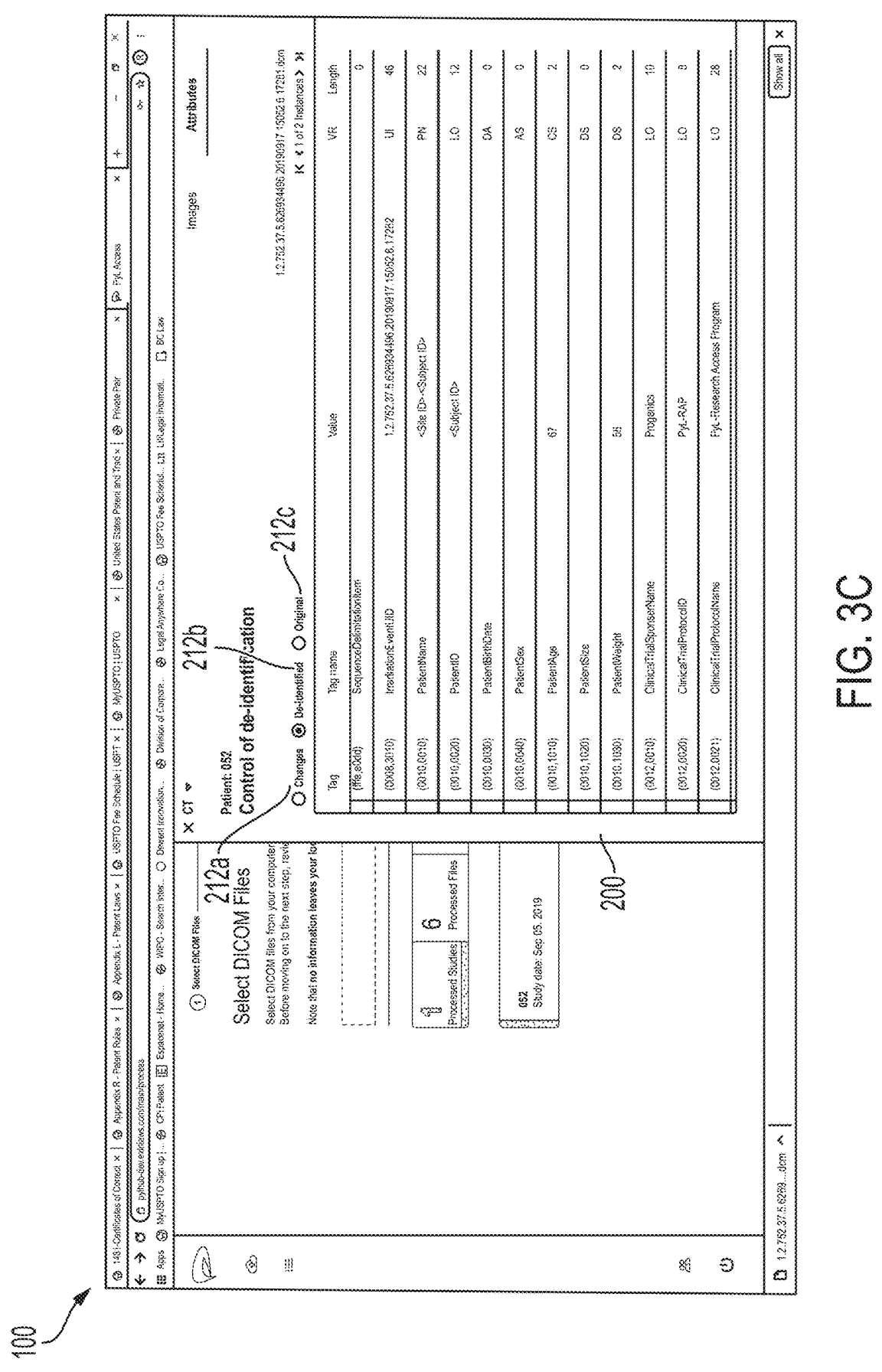
Figure 3D:
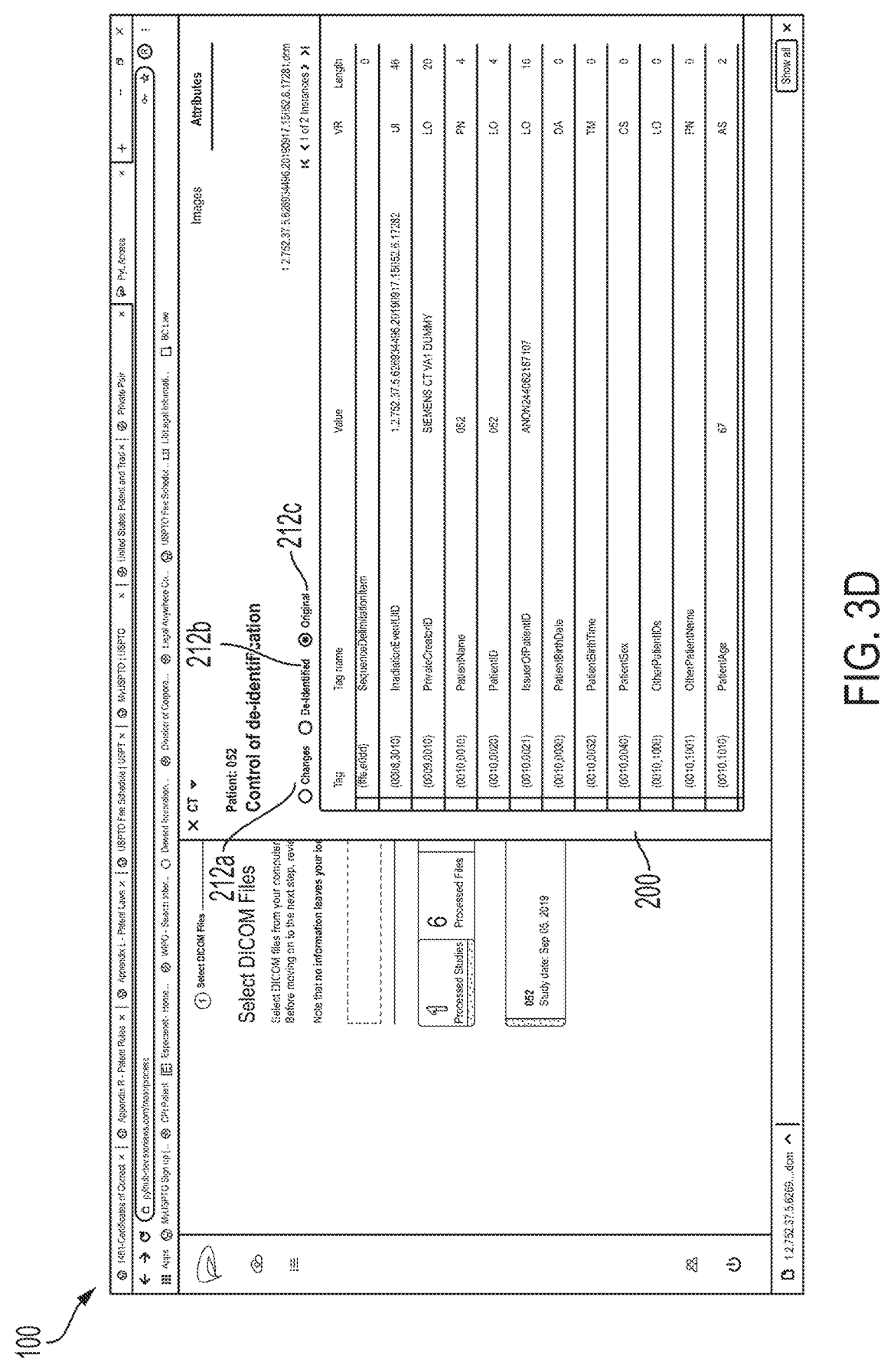

As shown in FIG. 3C and FIG. 3D, a user may also view de-identified metadata as well as the original metadata (e.g., for comparison) via buttons 212b and 212c, respectively.

A. iii. File Upload

Figure 4A:
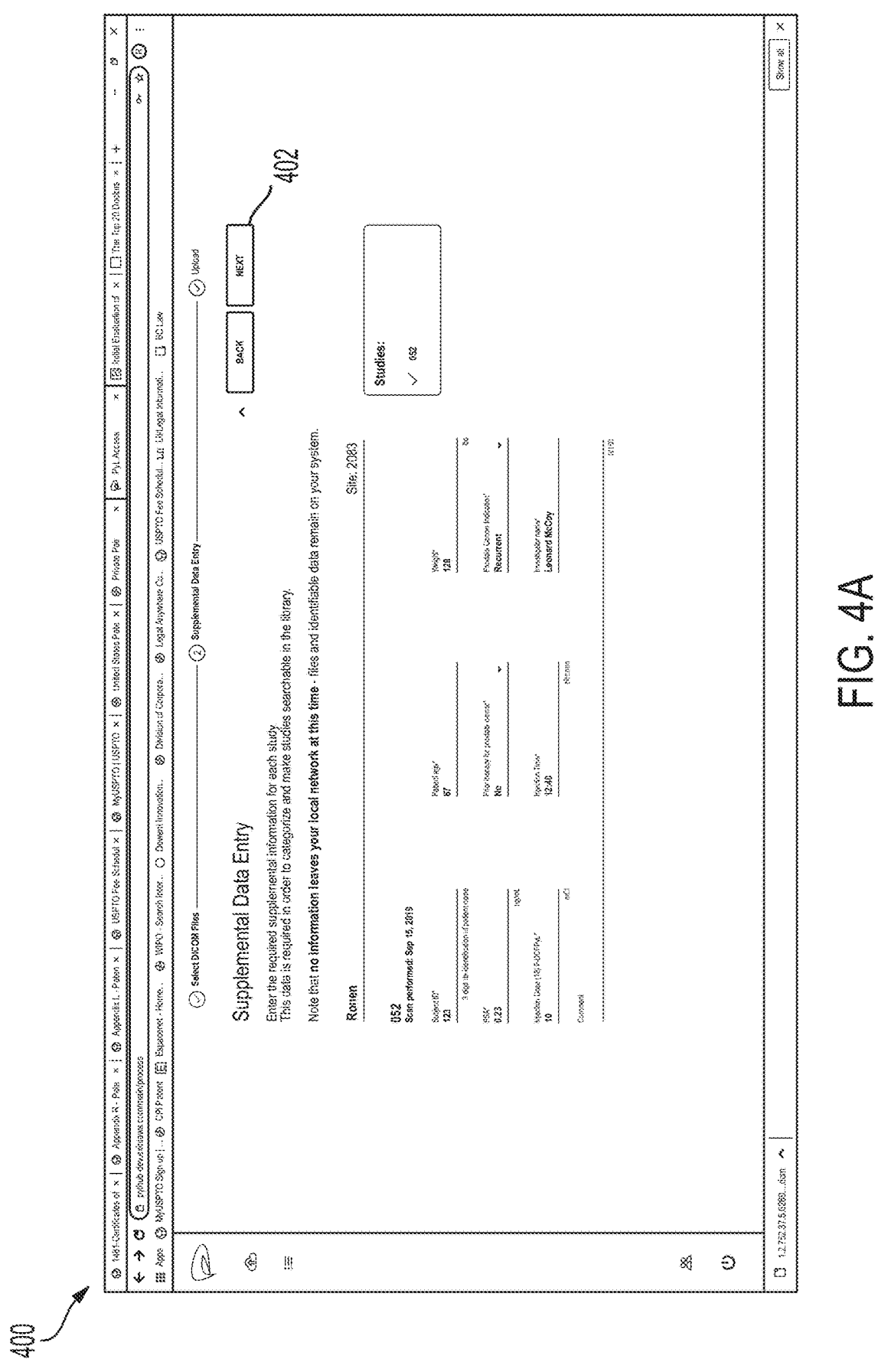
Figure 4B:
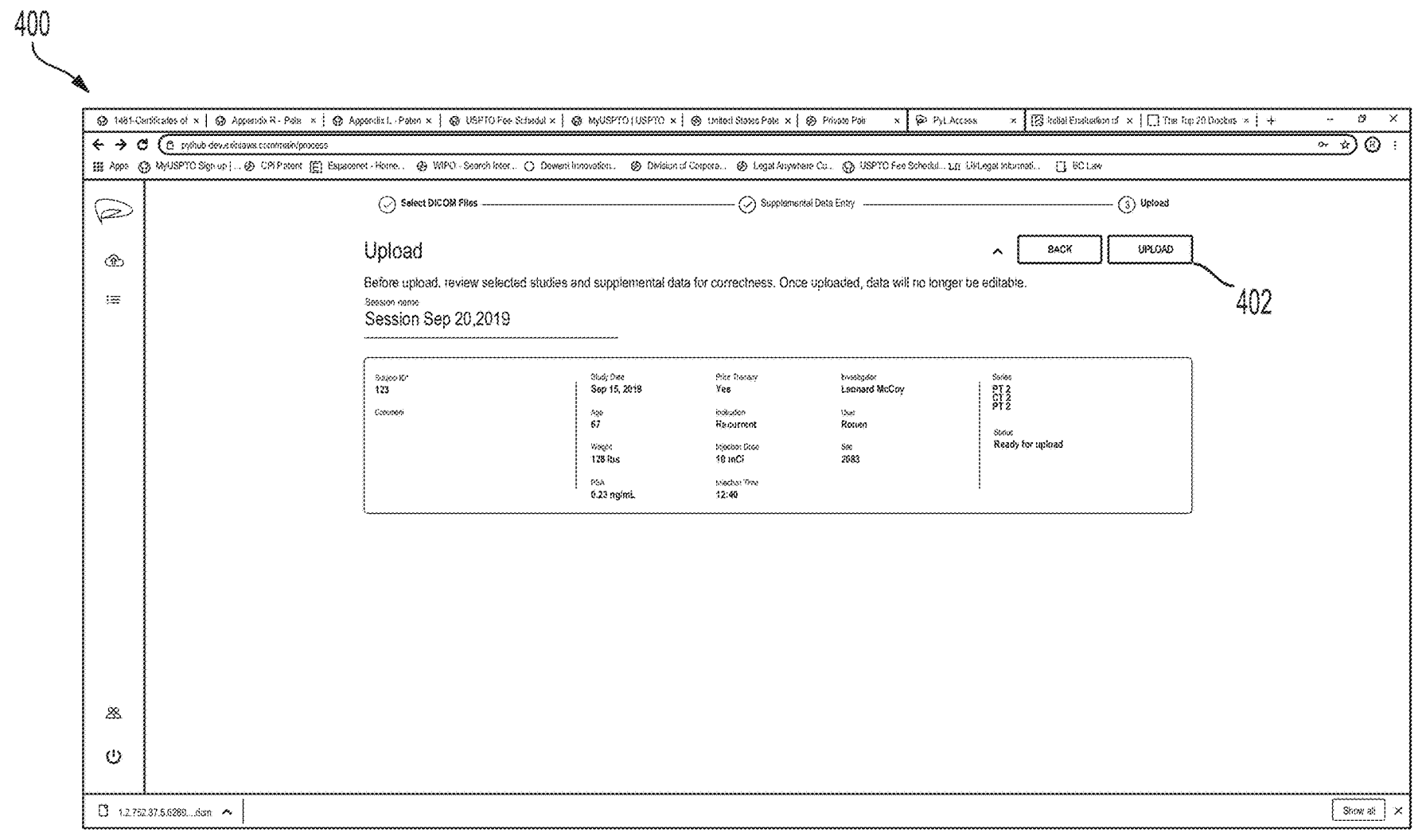
Figure 4C:
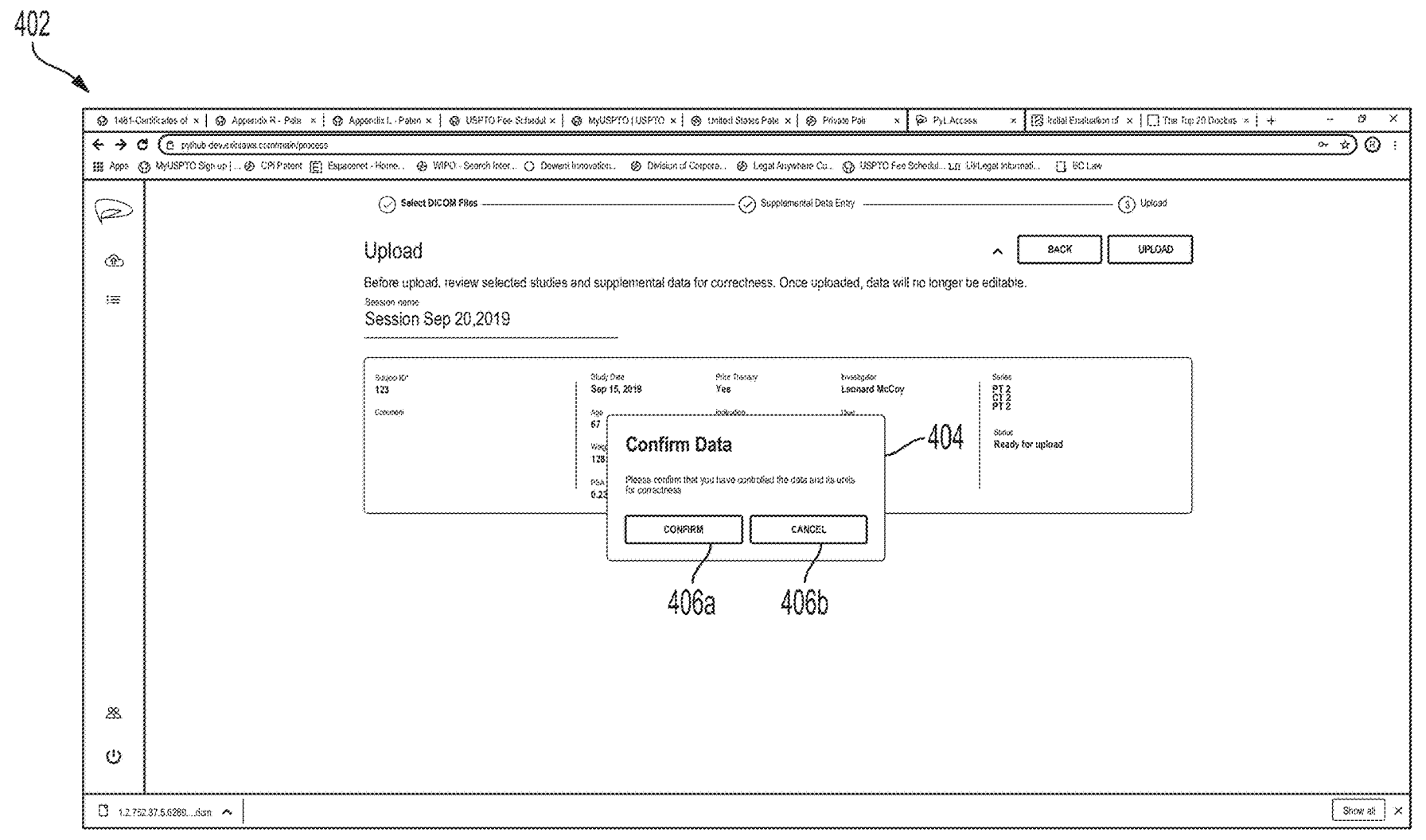
Figure 5:
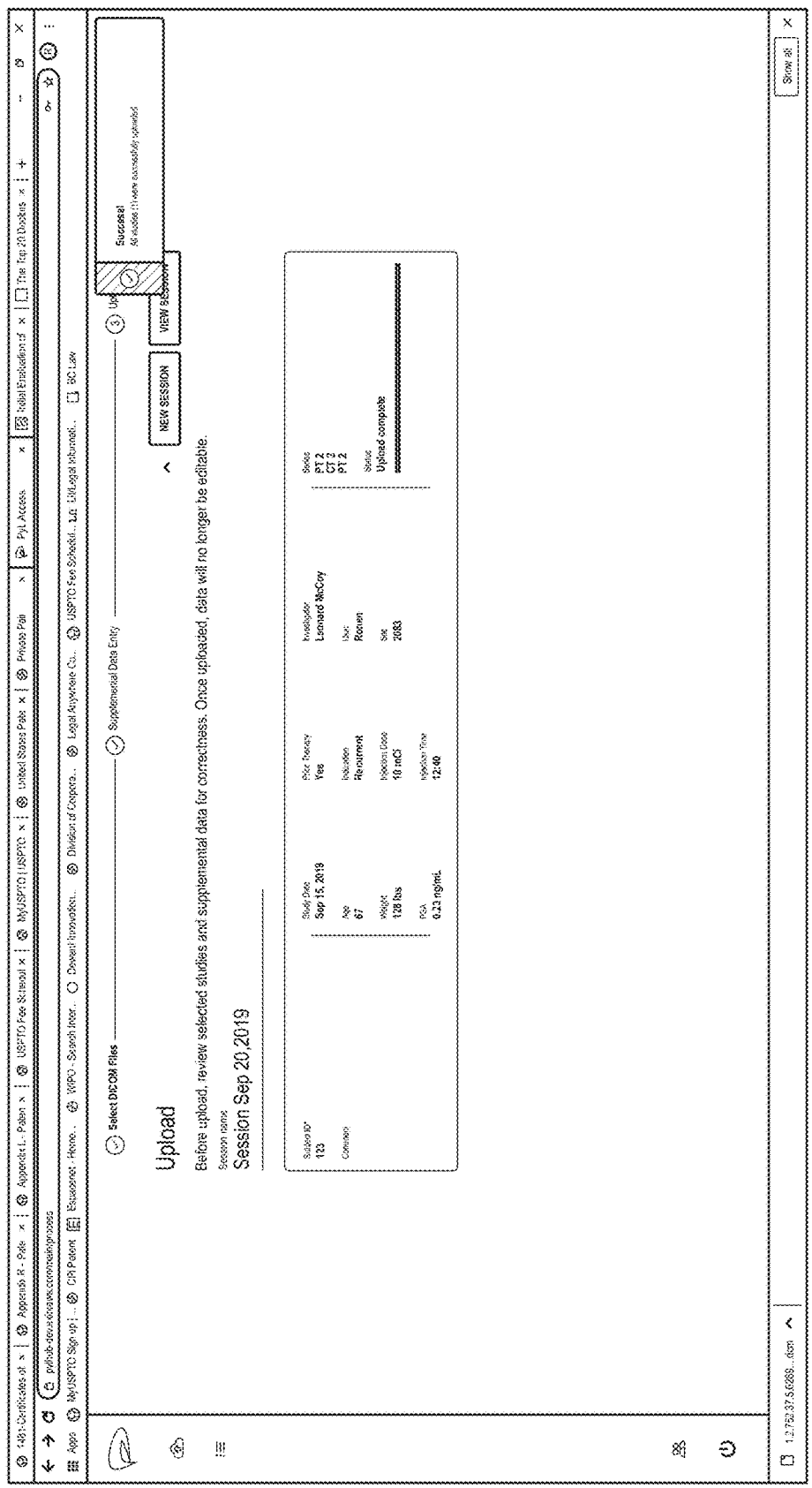
FIG. 5 is another screenshot of the view of the GUI shown in FIG. 4A, showing an indication of successful upload.

Turning to FIG. 4A, in certain embodiments, once a user has competed review of their selected files, a view appears 400 in which they are prompted to enter supplemental data for each study. Once the user enters supplemental data, they may be prompted to review the supplemental data as shown in FIG. 4B. The user may then initiate upload via button 402. As shown in FIG. 4C, in certain embodiments (e.g., as a precaution), a dialog box 404 is displayed requiring a user to confirm 406a the upload. The user may, alternatively, select cancel 406b to cancel the upload and return to the previous views of the GUI. Provided the user selects confirm 406a, the selected files are uploaded, with the original associated metadata replaced with corresponding de-identified metadata. FIG. 5 shows an example screen 500 displayed confirming successful completion of file upload.

As shown in FIGS. 6A-6D, once files are uploaded, a user may browse uploaded data to which they have permission to access. As shown in FIGS. 6A-6D, data may be organized and grouped according to studies. A user may search for particular data files in a flexible manner, by entering various criteria, such as a cancer indication (FIG. 6B), a diagnostic measurement value, such as a prostate specific membrane antigen (PSA) value (FIG. 6C), a particular imaging modality (FIG. 6D), and other parameters.

Figure 7B:
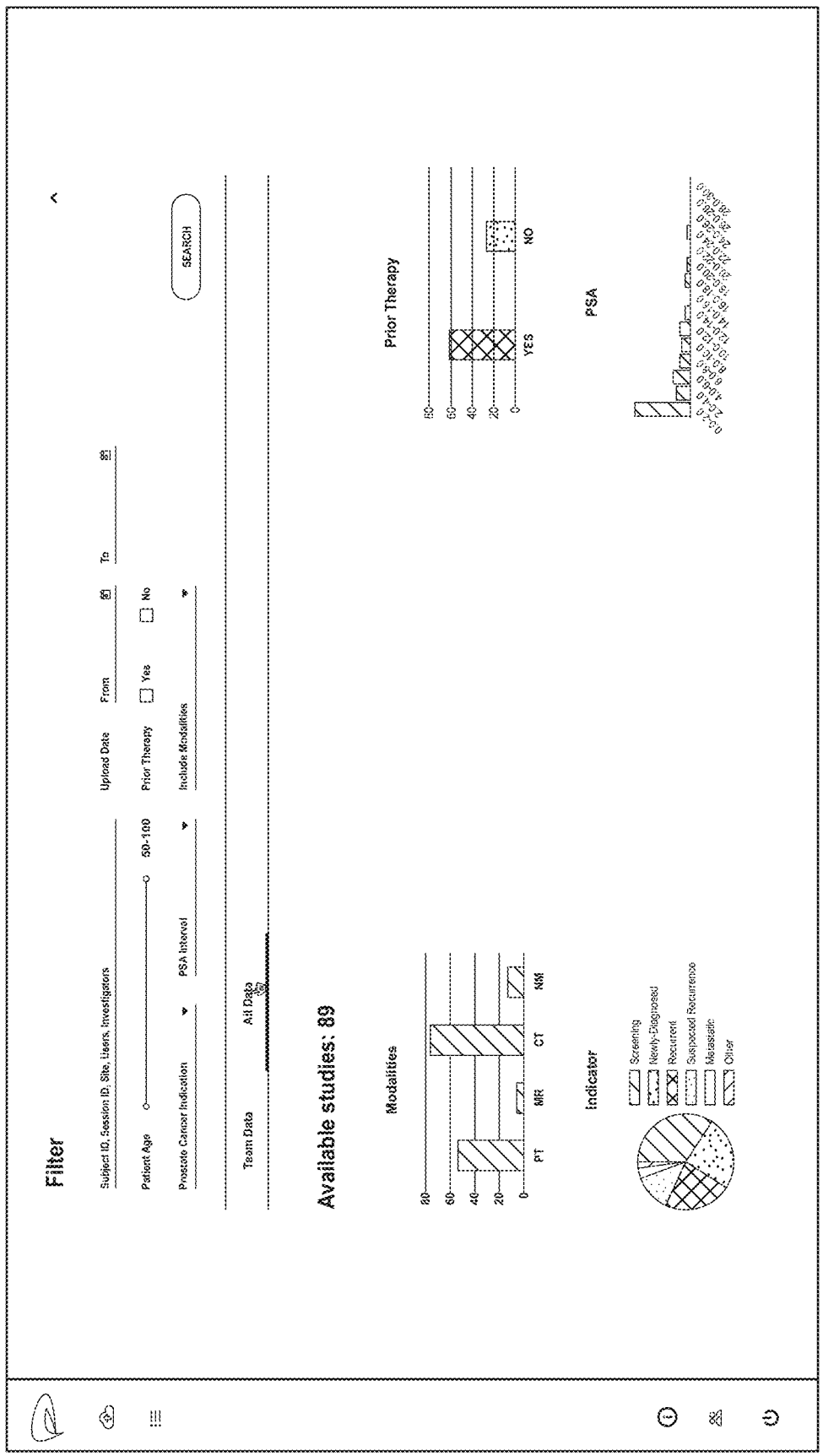
FIG. 7B is another screenshot of the GUI shown in FIG. 7A, showing a view that allows a user to interactively view and apply filters to graphical representations of study summary data from uploaded medical imaging studies.
Figure 7C:
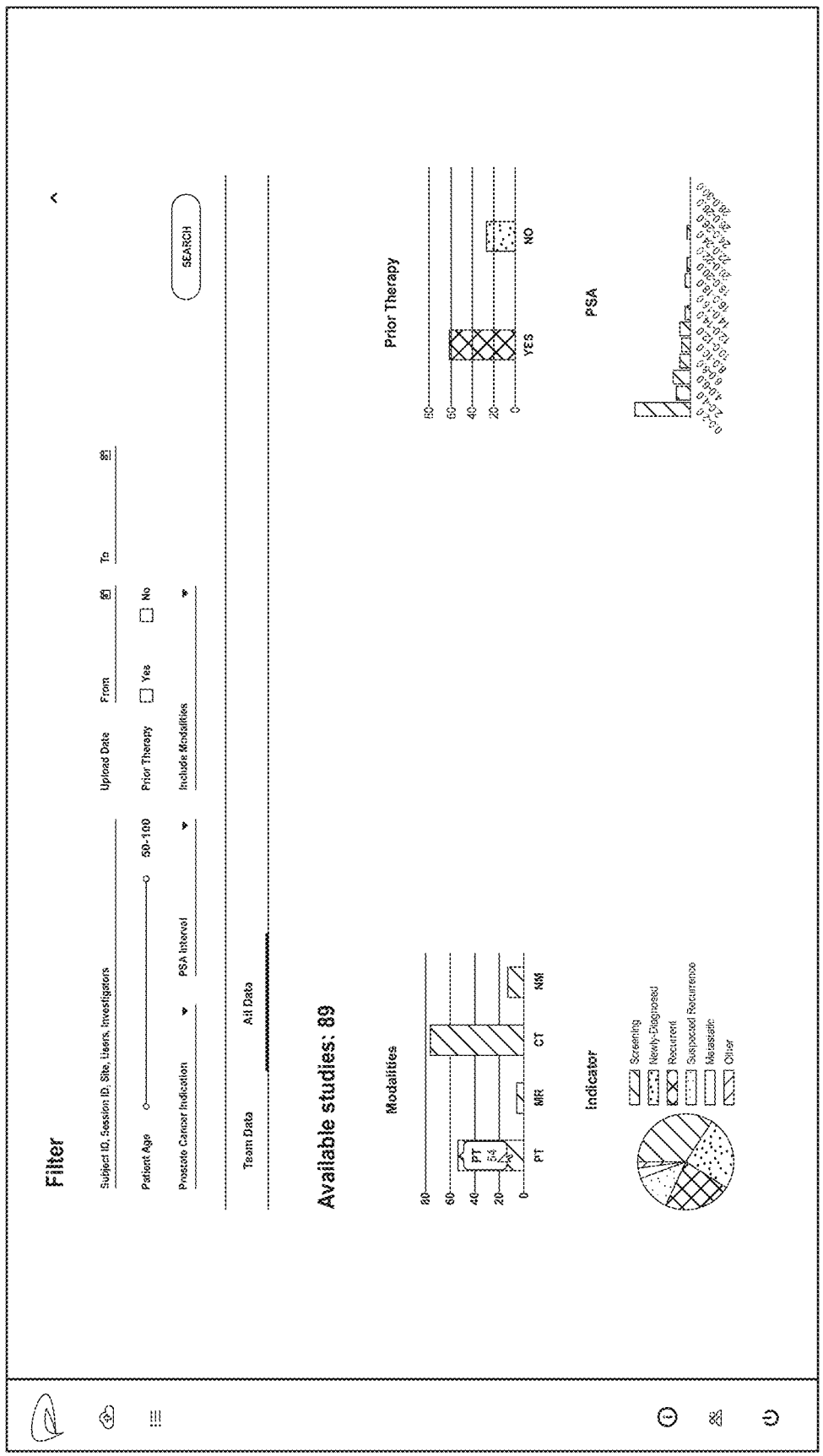
FIG. 7C is another screenshot of the view of the GUI shown in FIG. 7B, showing a user interaction with one of the graphical representations of study summary data.
Figure 7D:
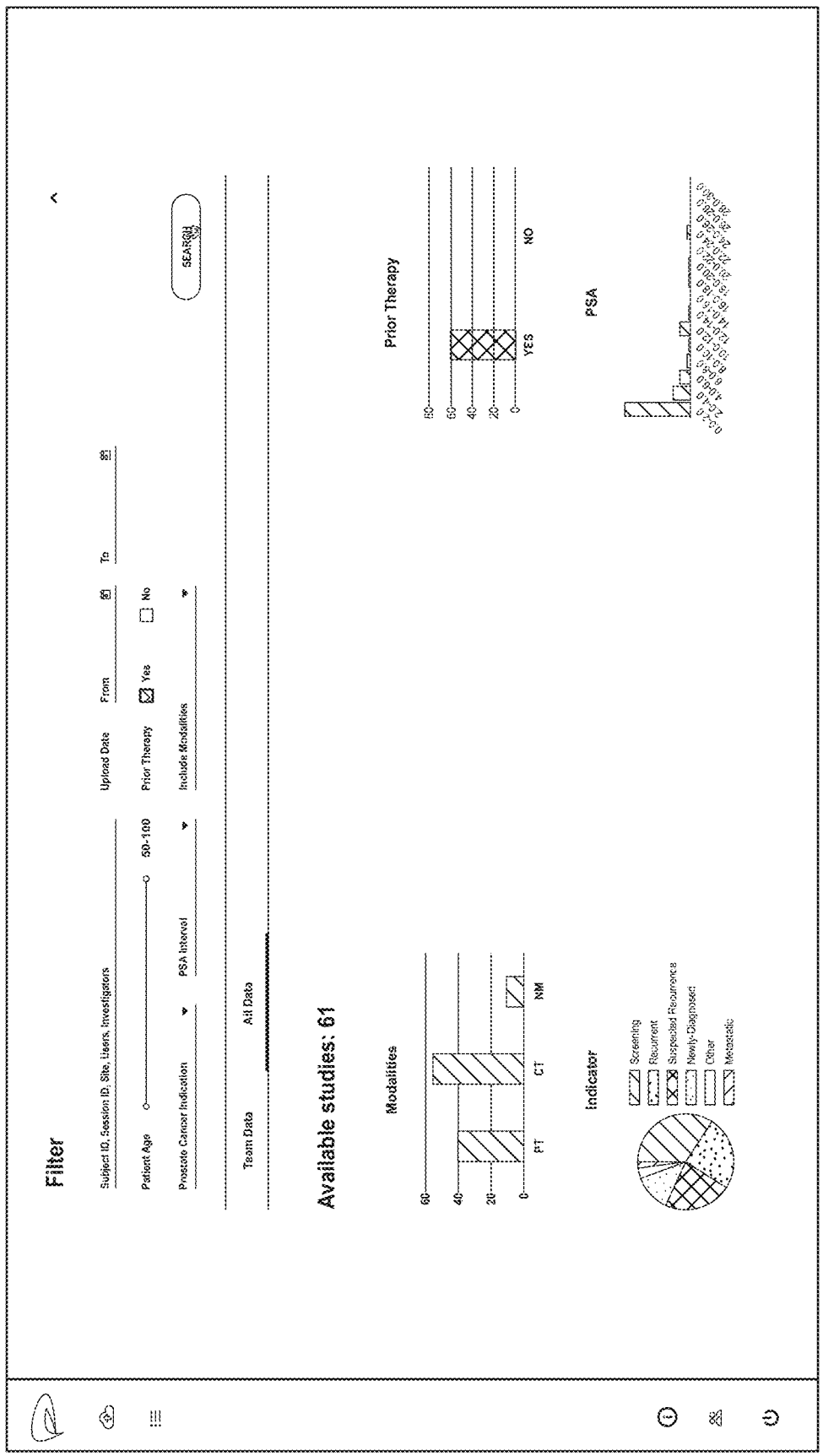
FIG. 7D is another screenshot of the view of the GUI shown in FIG. 7B, showing a updates to the graphical representations following filtering of data via a user interaction with a graphical filter control element.
Figure 7E:
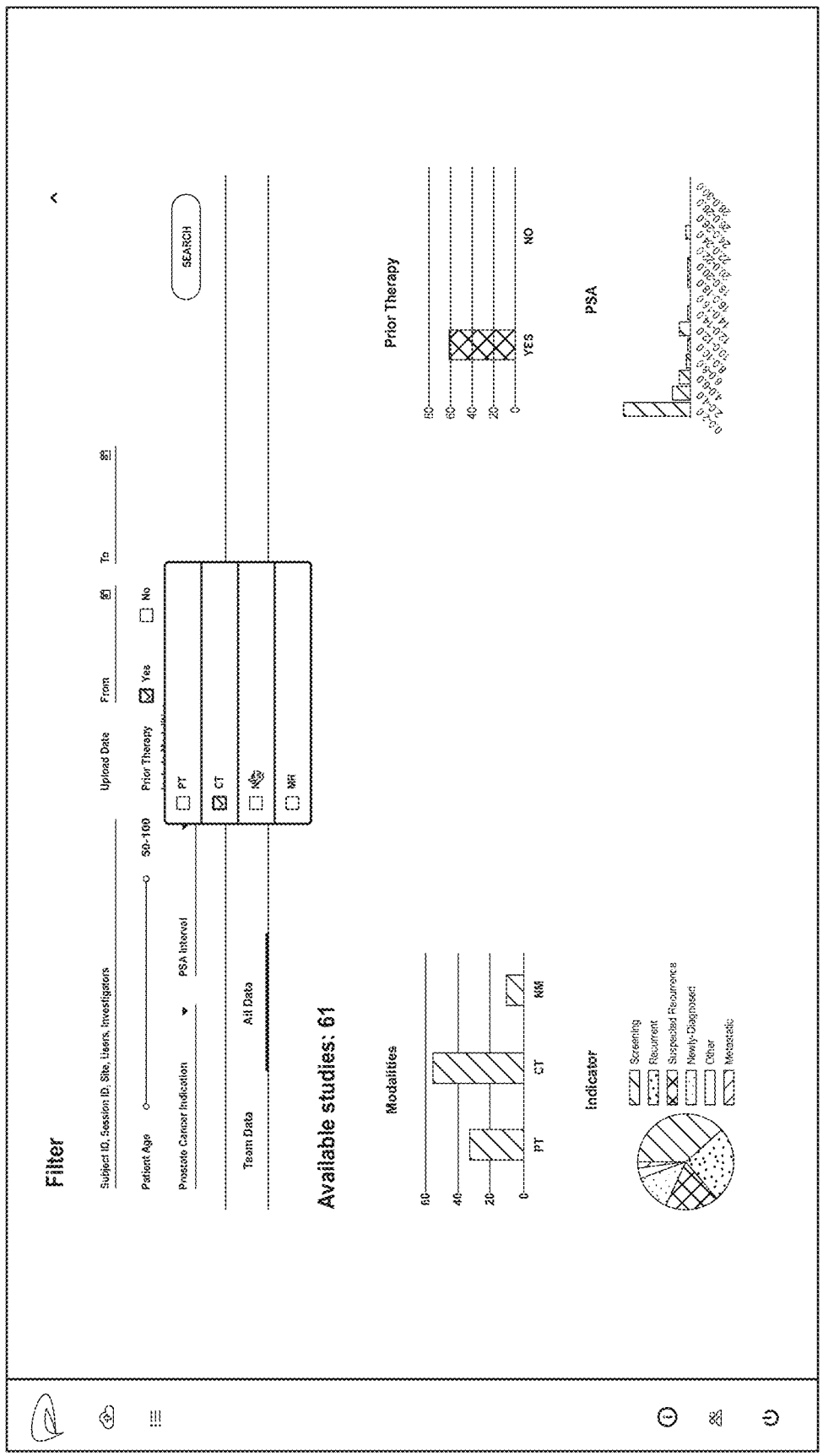
FIG. 7E is another screenshot of the view of the GUI shown in FIG. 7B, showing a user interaction with a graphical filter control element.
Figure 7F:
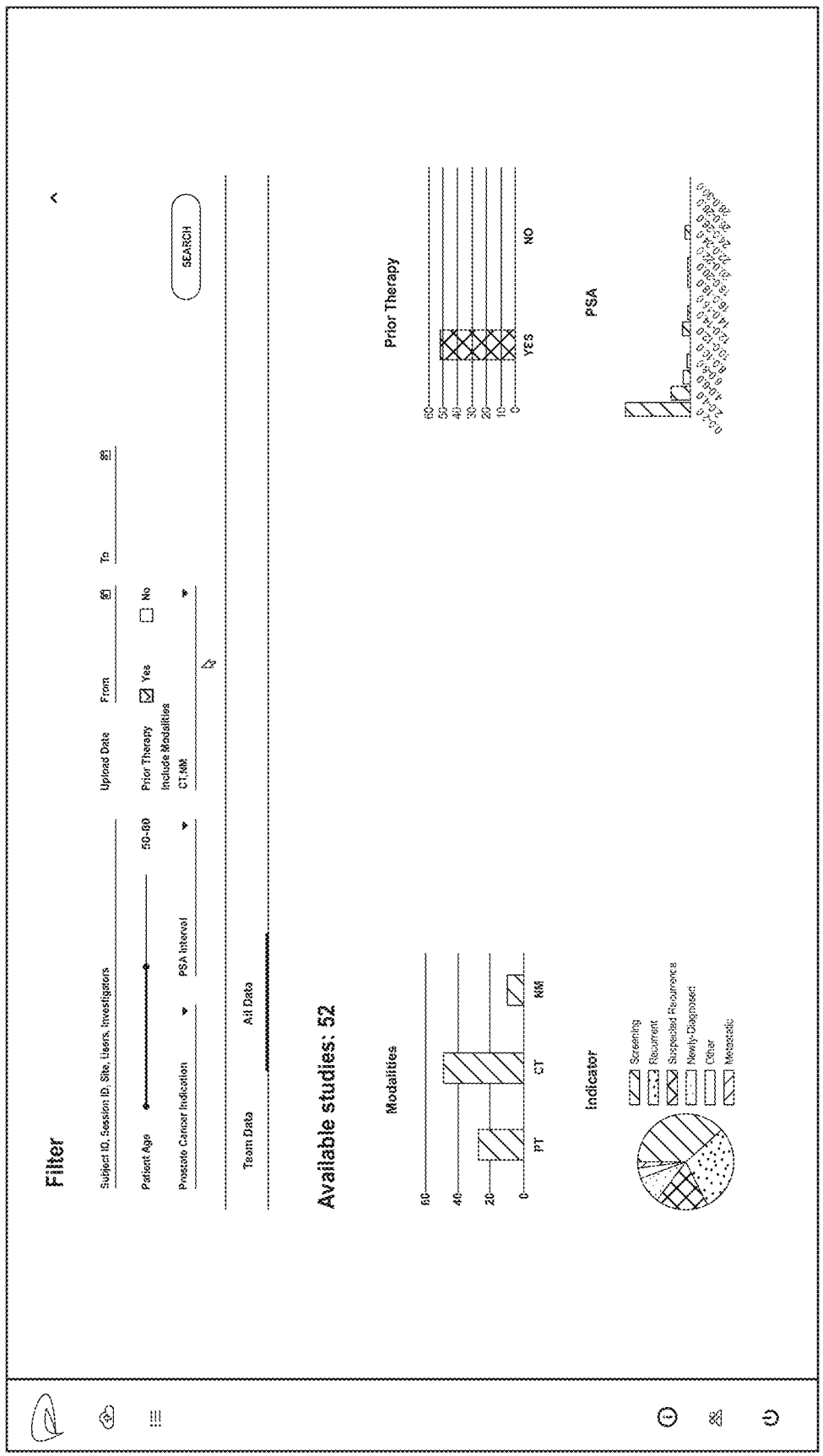
FIG. 7F is another screenshot of the view of the GUI shown in FIG. 7B, showing a updates to the graphical representations following filtering of data via a user interaction with a graphical filter control element.

Turning to FIGS. 7A-7F, a user may also (e.g., by selecting "All Data" as shown in FIG. 7A) view and interact with graphical representations of data summarizing the medical imaging studies uploaded to the cloud-based platform. As shown in FIGS. 7B-7F, the GUI allows a user to view distributions of study summary variables corresponding to prior therapy, prostate cancer indication, PSA interval, and imaging modality. The GUI comprises a plurality of graphical filter control elements each corresponding to a particular study summary variable. A user may use the graphical filter control elements to select sub-ranges of various study summary variables to use to filter the displayed graphical representations of the data distributions (as used in this sense, the term sub-range does not necessarily refer to a continuous range—it may be piece-wise continuous or, for, variables having a discrete set of values, a list of specific values).

Figure 8:
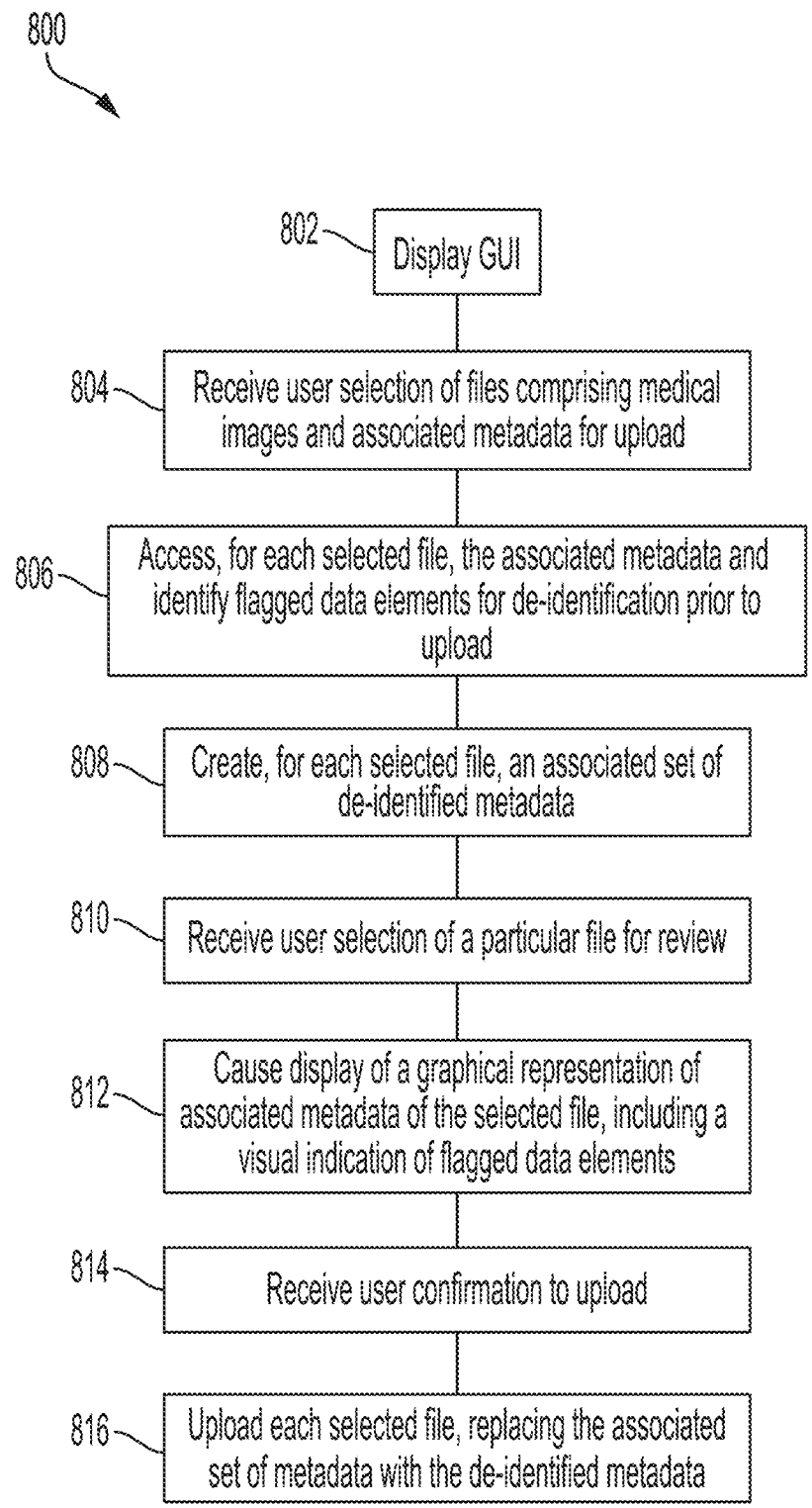
FIG. 8 is a block flow diagram of a process for secure upload of medical images and associated metadata from a local computing device to a network-based platform, according to an illustrative embodiment.

B. Processes for Displaying GUI Tools, Uploading De-Identified Medical Image Files, and Interactive Data Representation Display An example process 800 performed by a local computing device to providing interactive GUI tools that facilitate secure upload of files comprising medical images and associated metadata in accordance with the systems and methods described herein is shown in FIG. 8. In a first step 802, the local computing device causes display of the GUI that guides the user through image upload and allows them to review their data, as described herein. The processor receives (e.g., via the GUI) a user selection of files comprising medical images and associated metadata 804. The processor accesses, for each selected file, associated metadata of the file and identifies sensitive data elements to be flagged for de-identification prior to upload 806. The processor then creates, for each selected file de-identified metadata corresponding to the original associated metadata with values of the flagged data elements removed and/or masked.

In order to allow a user to review metadata and the de-identification process, a user selection of a particular file to review is received 810, and a graphical representation of associated metadata is caused to be displayed 812. For example, a graphical representation of metadata changes, such as the tabular displays shown in FIG. 3A and FIG. 3B may be presented to the user. These steps may be repeated for multiple sets of associated metadata of multiple files.

Once a user initiates and confirms 814 upload of the selected files, the original metadata of each selected file is replaced with the corresponding de-identified metadata and the files are uploaded 816.

Figure 9:
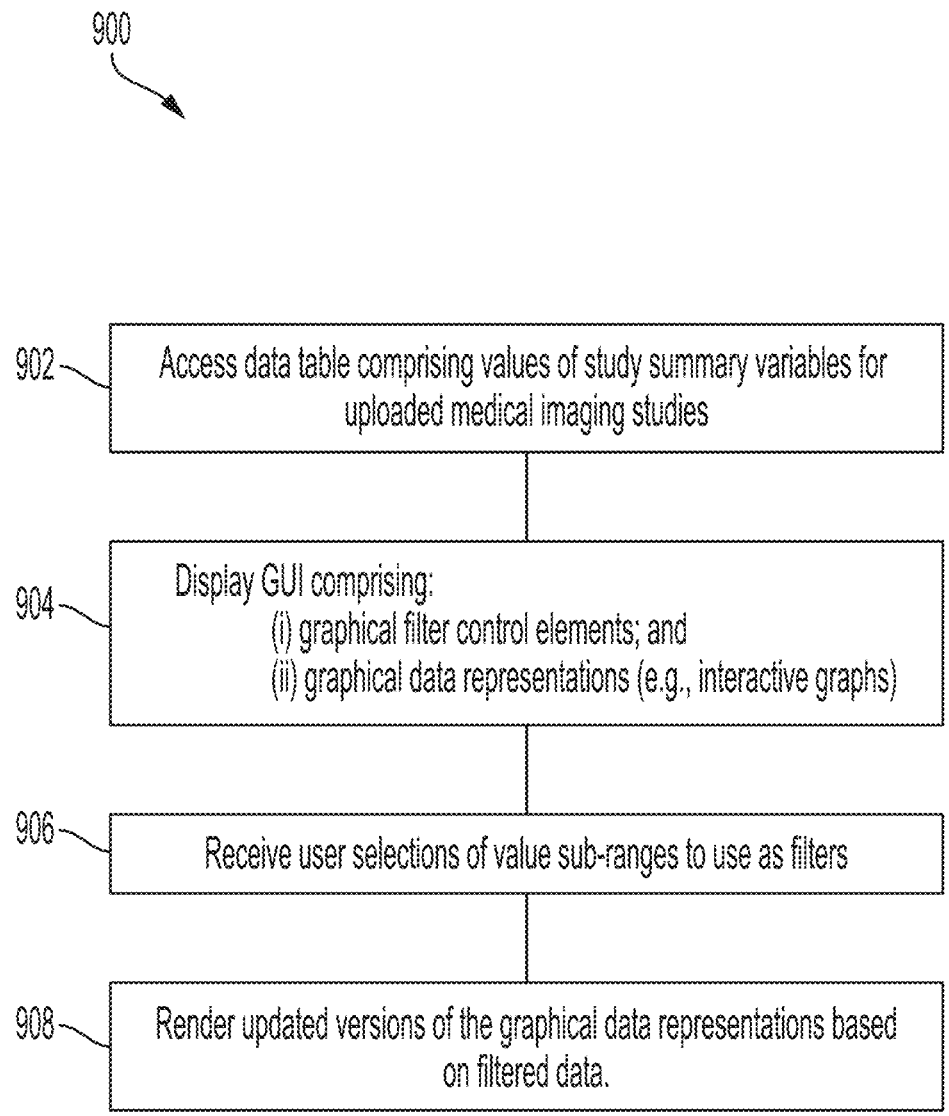
FIG. 9 is a block flow diagram of a processes for interactive display of data representing uploaded medical imaging studies, according to an illustrative embodiment.

Turning to FIG. 9, FIG. 9 is a block flow diagram of an example processes 9 for interactive display of data representing uploaded medical imaging studies, e.g., as described herein with respect to FIGS. 7A-7F. As shown in FIG. 9, a data table comprising values of study summary variables for uploaded medical imaging studies is accessed 902 and a GUI comprising graphical representations of the data is displayed 904. The displayed GUI also comprises graphical filter control elements that a user can use to adjust filters for controlling the data display. In particular, a user may select, via interaction with a graphical filter control element corresponding to a particular study summary variable, a sub-range of that variable to use as a filter 906. The selected sub-range is received, and used to filter data. Updated versions of the graphical data representations are then rendered 908 for display (e.g., to update the GUI).

C. Computer System and Network Environment

Figure 10:
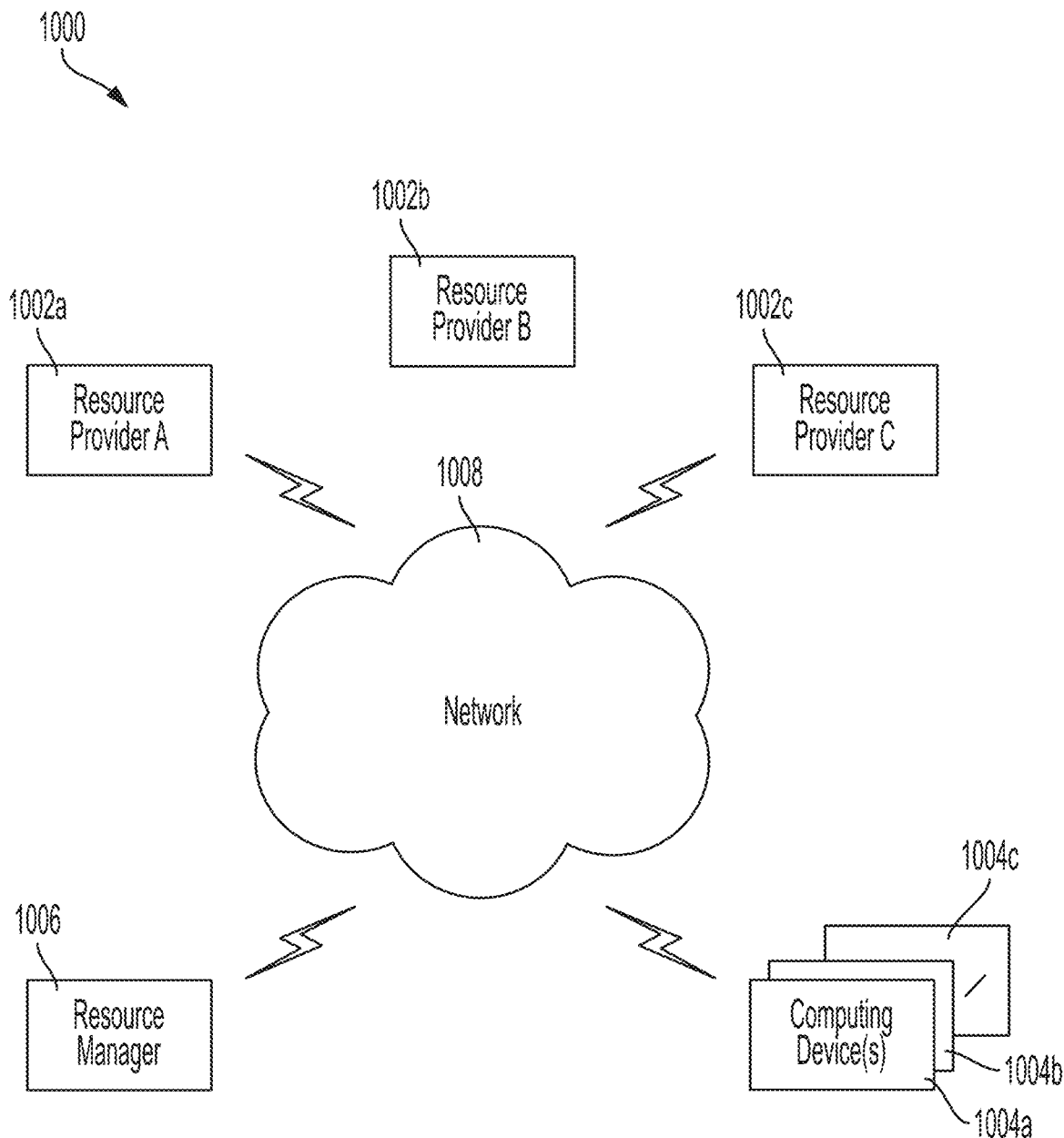
FIG. 10 is a block diagram of an exemplary cloud computing environment, used in certain embodiments.

As shown in FIG. 10, an implementation of a network environment 1000 for use in providing systems and methods described herein is shown and described. In brief overview, referring now to FIG. 10, a block diagram of an exemplary cloud computing environment 1000 is shown and described. The cloud computing environment 1000 may include one or more resource providers 1002a, 1002b, 1002c (collectively, 1002). Each resource provider 1002 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1002 may be connected to any other resource provider 1002 in the cloud computing environment 1000. In some implementations, the resource providers 1002 may be connected over a computer network 1008. Each resource provider 1002 may be connected to one or more computing device 1004a, 1004b, 1004c (collectively, 1004), over the computer network 1008.

The cloud computing environment 1000 may include a resource manager 1006. The resource manager 1006 may be connected to the resource providers 1002 and the computing devices 1004 over the computer network 1008. In some implementations, the resource manager 1006 may facilitate the provision of computing resources by one or more resource providers 1002 to one or more computing devices 1004. The resource manager 1006 may receive a request for a computing resource from a particular computing device 1004. The resource manager 1006 may identify one or more resource providers 1002 capable of providing the computing resource requested by the computing device 1004. The resource manager 1006 may select a resource provider 1002 to provide the computing resource. The resource manager 1006 may facilitate a connection between the resource provider 1002 and a particular computing device 1004. In some implementations, the resource manager 1006 may establish a connection between a particular resource provider 1002 and a particular computing device 1004. In some implementations, the resource manager 1006 may redirect a particular computing device 1004 to a particular resource provider 1002 with the requested computing resource.

Figure 11:
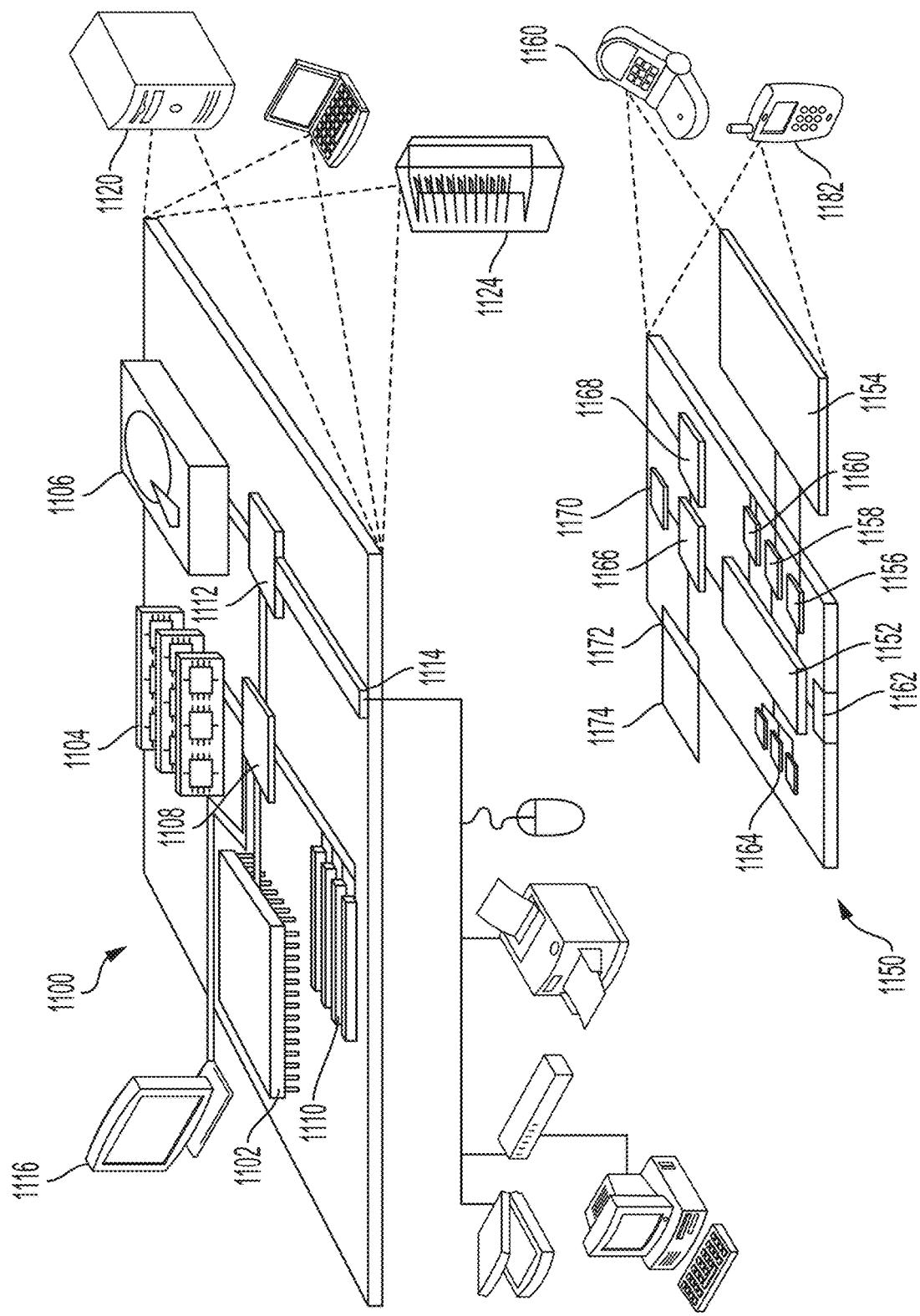
FIG. 11 is a block diagram of an example computing device and an example mobile computing device used in certain embodiments.

FIG. 11 shows an example of a computing device 1100 and a mobile computing device 1150 that can be used to implement the techniques described in this disclosure. The computing device 1100 is intended to represent various forms of digital computers, such as laptops, desktops, workstations, personal digital assistants, servers, blade servers, mainframes, and other appropriate computers. The mobile computing device 1150 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1100 includes a processor 1102, a memory 1104, a storage device 1106, a high-speed interface 1108 connecting to the memory 1104 and multiple high-speed expansion ports 1110, and a low-speed interface 1112 connecting to a low-speed expansion port 1114 and the storage device 1106. Each of the processor 1102, the memory 1104, the storage device 1106, the high-speed interface 1108, the high-speed expansion ports 1110, and the low-speed interface 1112, are interconnected using various busses, and may be mounted on a common motherboard or in other manners as appropriate. The processor 1102 can process instructions for execution within the computing device 1100, including instructions stored in the memory 1104 or on the storage device 1106 to display graphical information for a GUI on an external input/output device, such as a display 1116 coupled to the high-speed interface 1108. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 1104 stores information within the computing device 1100. In some implementations, the memory 1104 is a volatile memory unit or units. In some implementations, the memory 1104 is a non-volatile memory unit or units. The memory 1104 may also be another form of computer-readable medium, such as a magnetic or optical disk.

The storage device 1106 is capable of providing mass storage for the computing device 1100. In some implementations, the storage device 1106 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1102), perform one or more methods, such as those described above. The instructions can also be stored by one or more storage devices such as computer- or machine-readable mediums (for example, the memory 1104, the storage device 1106, or memory on the processor 1102).

The high-speed interface 1108 manages bandwidth-intensive operations for the computing device 1100, while the low-speed interface 1112 manages lower bandwidth-intensive operations. Such allocation of functions is an example only. In some implementations, the high-speed interface 1108 is coupled to the memory 1104, the display 1116 (e.g., through a graphics processor or accelerator), and to the high-speed expansion ports 1110, which may accept various expansion cards (not shown). In the implementation, the low-speed interface 1112 is coupled to the storage device 1106 and the low-speed expansion port 1114. The low-speed expansion port 1114, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1100 may be implemented in a number of different forms, as shown in the figure. For example, it may be implemented as a standard server 1120, or multiple times in a group of such servers. In addition, it may be implemented in a personal computer such as a laptop computer 1122. It may also be implemented as part of a rack server system 1124. Alternatively, components from the computing device 1100 may be combined with other components in a mobile device (not shown), such as a mobile computing device 1150. Each of such devices may contain one or more of the computing device 1100 and the mobile computing device 1150, and an entire system may be made up of multiple computing devices communicating with each other.

The mobile computing device 1150 includes a processor 1152, a memory 1164, an input/output device such as a display 1154, a communication interface 1166, and a transceiver 1168, among other components. The mobile computing device 1150 may also be provided with a storage device, such as a micro-drive or other device, to provide additional storage. Each of the processor 1152, the memory 1164, the display 1154, the communication interface 1166, and the transceiver 1168, are interconnected using various buses, and several of the components may be mounted on a common motherboard or in other manners as appropriate.

The processor 1152 can execute instructions within the mobile computing device 1150, including instructions stored in the memory 1164. The processor 1152 may be implemented as a chipset of chips that include separate and multiple analog and digital processors. The processor 1152 may provide, for example, for coordination of the other components of the mobile computing device 1150, such as control of user interfaces, applications run by the mobile computing device 1150, and wireless communication by the mobile computing device 1150.

The processor 1152 may communicate with a user through a control interface 1158 and a display interface 1156 coupled to the display 1154. The display 1154 may be, for example, a TFT (Thin-Film-Transistor Liquid Crystal Display) display or an OLED (Organic Light Emitting Diode) display, or other appropriate display technology. The display interface 1156 may comprise appropriate circuitry for driving the display 1154 to present graphical and other information to a user. The control interface 1158 may receive commands from a user and convert them for submission to the processor 1152. In addition, an external interface 1162 may provide communication with the processor 1152, so as to enable near area communication of the mobile computing device 1150 with other devices. The external interface 1162 may provide, for example, for wired communication in some implementations, or for wireless communication in other implementations, and multiple interfaces may also be used.

The memory 1164 stores information within the mobile computing device 1150. The memory 1164 can be implemented as one or more of a computer-readable medium or media, a volatile memory unit or units, or a non-volatile memory unit or units. An expansion memory 1174 may also be provided and connected to the mobile computing device 1150 through an expansion interface 1172, which may include, for example, a SIMM (Single In Line Memory Module) card interface. The expansion memory 1174 may provide extra storage space for the mobile computing device 1150, or may also store applications or other information for the mobile computing device 1150. Specifically, the expansion memory 1174 may include instructions to carry out or supplement the processes described above, and may include secure information also. Thus, for example, the expansion memory 1174 may be provide as a security module for the mobile computing device 1150, and may be programmed with instructions that permit secure use of the mobile computing device 1150. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 1152), perform one or more methods, such as those described above. The instructions can also be stored by one or more storage devices, such as one or more computer- or machine-readable mediums (for example, the memory 1164, the expansion memory 1174, or memory on the processor 1152). In some implementations, the instructions can be received in a propagated signal, for example, over the transceiver 1168 or the external interface 1162.

The mobile computing device 1150 may communicate wirelessly through the communication interface 1166, which may include digital signal processing circuitry where necessary. The communication interface 1166 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1168 using a radio-frequency. In addition, short-range communication may occur, such as using a Bluetooth®, Wi-Fi™, or other such transceiver (not shown). In addition, a GPS (Global Positioning System) receiver module 1170 may provide additional navigation- and location-related wireless data to the mobile computing device 1150, which may be used as appropriate by applications running on the mobile computing device 1150.

The mobile computing device 1150 may also communicate audibly using an audio codec 1160, which may receive spoken information from a user and convert it to usable digital information. The audio codec 1160 may likewise generate audible sound for a user, such as through a speaker, e.g., in a handset of the mobile computing device 1150. Such sound may include sound from voice telephone calls, may include recorded sound (e.g., voice messages, music files, etc.) and may also include sound generated by applications operating on the mobile computing device 1150.

The mobile computing device 1150 may be implemented in a number of different forms, as shown in the figure. For example, it may be implemented as a cellular telephone 1180. It may also be implemented as part of a smart-phone 1182, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, modules described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for secure upload of one or more medical images and associated metadata from a local computing device to a network-based analysis or decision support platform, the method comprising:
    (a) causing, by a processor of the local computing device, display of a graphical user interface (GUI) for user review and management of medical image upload;
    (b) receiving, by the processor of the local computing device, a user selection of one or more files for upload, wherein each of the one or more files for upload comprises one or more medical images and associated metadata comprising a plurality of data elements, and wherein each selected file is stored on the local computing device;

(c) accessing, by the processor of the local computing device, for each selected file, the associated metadata of the file and identifying, among the plurality of data elements of the associated metadata, one or more flagged data elements for de-identification prior to upload;

(d) creating, by the processor of the local computing device, for each selected file, de-identified metadata corresponding to the associated metadata of the file with values of the flagged data elements removed or masked;

(e) receiving, by the processor of the local computing device, a user selection of a particular file for review of de-identification;

(f) responsive to the user selection of the particular file, causing, by the processor of the local computing device, display of a graphical representation of metadata changes comprising a listing of the plurality of data elements of the associated metadata of the particular file and a visual indication of the one or more flagged data elements, wherein the visual indication visually distinguishes the one or more flagged data elements from other data elements;

(g) receiving, by the processor of the local computing device, a user confirmation to upload; and (h) uploading, by the processor of the local computing device, each selected file with the original associated metadata replaced with the corresponding de-identified metadata, to the network-based platform.

2. The method of claim 1, comprising:
(i) causing, by the processor, display of a graphical representation of the de-identified metadata that corresponds to the associated metadata of the particular file.

3. The method of claim 1, comprising
(j) causing, by the processor, display of a graphical representation of original associated metadata of the particular file.

4. The method of claim 1, wherein at least a portion of the flagged data elements are identified as elements to be masked by, for each element to be masked, replacing an initial value of the element to be masked with a particular masking value, and wherein the graphical representation of metadata changes further comprises, for each element to be masked, an indication of the initial value of the element and an indication of the particular masking value for the element.

5. The method of claim 1, wherein, in the graphical representation of metadata changes, the listing of the plurality of data elements of the associated metadata is displayed in a table.

6. The method of claim 5, wherein each flagged data element is identified via a color coded icon.

7. The method of claim 1, wherein at least a portion of the flagged data elements are identified as elements to be masked and wherein step (c) comprises, for each element to be masked, replacing an initial value of the element to be masked with a particular masking value.

8. The method of claim 1, wherein step (c) comprises accessing, by the processor, a stored de-identification protocol comprising a listing of data elements to flag.

9. The method of claim 1, further comprising:
receiving, by the processor, a user selection of one or more additional data elements to flag for de-identification; and
updating, by the processor, the de-identified set of metadata associated with each medical image to remove or mask a value of each selected additional data element.

10. The method of claim 1, wherein the one or more flagged data elements comprise one or more members selected from the group consisting of: a patient name, a patient identifier, a patient birth date.

11. The method of claim 1, wherein the local computing device is in communication with an imaging system.

12. The method of claim 1, wherein the local computing device is on a local network that is not part of the network-based analysis or decision support platform.

13. The method of claim 1 comprising:
following step (b), performing, by the processor of the local computing device, a pre-processing step to validate each of the one or more selected files for upload.

14. The method of claim 13, wherein:
the pre-processing step comprises identifying, for each file, a corresponding study to which the file belongs, thereby identifying one or more processed studies; and
the method comprises causing, by the processor of the local computing device, display of a graphical representation of processed studies comprising a listing of the one or more processed studies.

15. The method of claim 14, wherein the graphical representation of processed studies comprises, for each processed study, a visual indication of a number of different files of the study along with a visual indication of one or more imaging modalities used to obtain medical images of the files belonging to the study.

16. The method of claim 15, comprising:
receiving, by the processor of the local computing device, a user input to review images of a particular study; and
causing, by the processor of the local computing device, display of a first medical image of a first file and corresponding to a particular imaging modality, along with a graphical control element that allows the user to view additional images (i) of files belong to the particular study and (ii) also corresponding to the particular imaging modality.

17. The method of claim 1, wherein the graphical representation of metadata changes comprises one or more color coded icons in proximity to the flagged data elements.

18. A system for secure upload of one or more medical images and associated metadata from a local computing device to a network-based analysis or decision support platform, the system comprising:
a processor of the local computing device; and
a memory having instructions stored thereon, wherein the instructions, when executed by the processor, cause the processor to:
(a) cause display of a graphical user interface (GUI) for user review and management of medical image upload;
(b) receive a user selection of one or more files for upload, wherein each of the one or more files for upload comprises one or more medical images and associated metadata comprising a plurality of data elements, and wherein each selected file is stored on the local computing device;
(c) access, for each selected file, the associated metadata of the file and identifying, among the plurality of data elements of the associated metadata, one or more flagged data elements for de-identification prior to upload;

(d) create, for each selected file, de-identified metadata corresponding to the associated metadata of the file with values of the flagged data elements removed or masked;

(e) receive a user selection of a particular file for review of de-identification;

(f) responsive to the user selection of the particular file, cause display of a graphical representation of metadata changes comprising a listing of the plurality of data elements of the associated metadata of the particular file and a visual indication of the one or more flagged data elements, wherein the visual indication visually distinguishes the one or more flagged data elements from other data elements;

(g) receive a user confirmation to upload; and (h) upload each selected file with the original associated metadata replaced with the corresponding de-identified metadata, to the network-based platform.

19. The system of claim 18, wherein the local computing device is in communication with an imaging system.

20. The system of claim 19, further comprising the imaging system.

21. The system of claim 18, wherein the local computing device is on a local network that is not part of the network-based analysis or decision support platform.

22. The system of claim 18, wherein the graphical representation of metadata changes comprises one or more color coded icons in proximity to the flagged data elements.

23. The system of claim 18, wherein, in the graphical representation of metadata changes, the listing of the plurality of data elements of the associated metadata is displayed in a table in which each flagged data element is identified via a color coded icon.

* * * * *